(12) United States Patent
Nakamura

(10) Patent No.: US 8,744,149 B2
(45) Date of Patent: Jun. 3, 2014

(54) MEDICAL IMAGE PROCESSING APPARATUS AND METHOD AND COMPUTER-READABLE RECORDING MEDIUM FOR IMAGE DATA FROM MULTIPLE VIEWPOINTS

(75) Inventor: Keigo Nakamura, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 746 days.

(21) Appl. No.: 12/895,270

(22) Filed: Sep. 30, 2010

(65) Prior Publication Data

US 2011/0075901 A1 Mar. 31, 2011

(30) Foreign Application Priority Data

Sep. 30, 2009 (JP) .................................. 2009-225778
Mar. 23, 2010 (JP) .................................. 2010-065404

(51) Int. Cl.
*G06K 9/00* (2006.01)

(52) U.S. Cl.
USPC ......................................................... 382/128

(58) Field of Classification Search
USPC ............ 600/300, 407; 128/920; 382/100, 128, 382/129, 130, 131, 132, 133, 134, 173, 382/181; 378/1, 37, 21, 41, 42, 38, 44, 51, 378/62, 65, 146
See application file for complete search history.

(56) References Cited

U.S. PATENT DOCUMENTS

| 7,058,210 | B2 | 6/2006 | Mundy et al. | |
|---|---|---|---|---|
| 7,859,543 | B2 * | 12/2010 | Salvador | 345/581 |
| 2005/0226405 | A1 | 10/2005 | Fukatsu et al. | |
| 2007/0064984 | A1 * | 3/2007 | Vassa et al. | 382/128 |
| 2007/0238948 | A1 * | 10/2007 | Bartsch et al. | 600/407 |
| 2008/0031503 | A1 * | 2/2008 | Kanada et al. | 382/128 |

(Continued)

FOREIGN PATENT DOCUMENTS

| JP | 2000-135215 A | 5/2000 |
|---|---|---|
| JP | 2001-137230 A | 5/2001 |

(Continued)

OTHER PUBLICATIONS

Takaharu et al., Japanese Publication No. 2010-211749, Case Image Retrieval Device, Method and Program, Cited by Applicant on IDS submitted on Sep. 30, 2010, Translation retrieved by Patent Abstracts of Japan, Date of publication of application: Sep. 24, 2010.*

(Continued)

*Primary Examiner* — Tahmina Ansari
(74) *Attorney, Agent, or Firm* — Sughrue Mion, PLLC

(57) ABSTRACT

A target-viewpoint position in a first-medical-image having multiple viewpoints is determined. Information about an anatomical structure and/or a lesion in the first-medical-image is obtained, as first information. Further, information about an anatomical structure and/or a lesion in a finding with respect to at least one second-medical-image of the same examined person as the first-medical-image, the information being related to the first information, is obtained, as second information, from image-reading-report information including the finding. Each of the at least one second-medical-image has multiple viewpoints, and was obtained at different time from the first-medical-image. The image-reading-report information is correlated with an image of a viewpoint position at which the finding was prepared. An image of a corresponding viewpoint position, which corresponds to the target-viewpoint position, is determined based on the viewpoint position of the image correlated with the image-reading-report information from which the second information has been obtained.

17 Claims, 15 Drawing Sheets

(56) References Cited

U.S. PATENT DOCUMENTS

| | | | |
|---|---|---|---|
| 2008/0166070 A1* | 7/2008 | Kariathungal et al. | 382/305 |
| 2008/0267481 A1 | 10/2008 | Nakamura | |
| 2010/0054555 A1* | 3/2010 | Owen | 382/128 |
| 2011/0075901 A1* | 3/2011 | Nakamura | 382/128 |
| 2012/0250961 A1* | 10/2012 | Iwasaki | 382/128 |
| 2013/0114867 A1* | 5/2013 | Kondo et al. | 382/128 |

FOREIGN PATENT DOCUMENTS

| | | |
|---|---|---|
| JP | 2002-045807 A | 2/2002 |
| JP | 2002253545 A | 9/2002 |
| JP | 2005027978 A | 2/2005 |
| JP | 2006-198032 A | 8/2006 |
| JP | 2007-289335 A | 11/2007 |
| JP | 2007-312837 A | 12/2007 |
| JP | 2008077163 A | 4/2008 |

OTHER PUBLICATIONS

Kazunari et al., Japanese Patent Application Publication JP 2005027978, Translation obtained by Patents Abstract of Japan, Date of Publication: Feb. 3, 2005, Date Accessed Dec. 27, 2013.*

Office Action issued on Sep. 17, 2013 in Japanese Patent Application No. 2010-065404.

Office Action dated Mar. 25, 2014, issued by the Japanese Patent and Trademark Office in counterpart Japanese Patent Application No. 2010-065404.

* cited by examiner

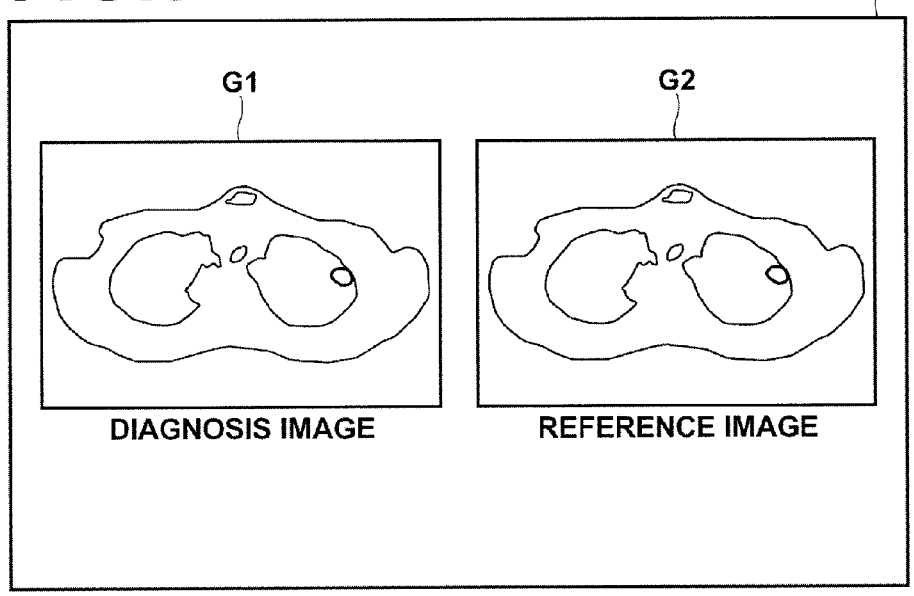
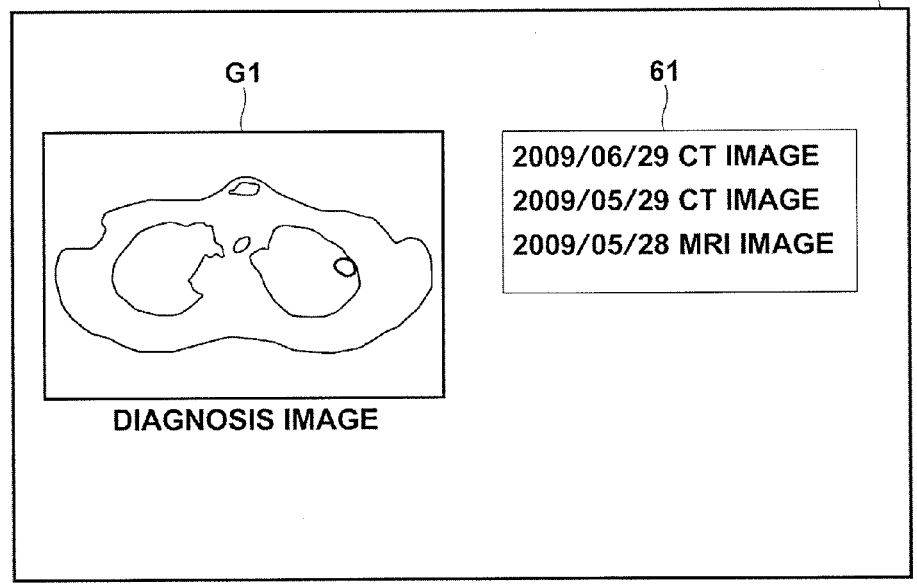

G11 DIAGNOSIS IMAGE  G12 REFERENCE IMAGE

G21 DIAGNOSIS IMAGE  G22 REFERENCE IMAGE

MEDICAL IMAGE PROCESSING APPARATUS AND METHOD AND COMPUTER-READABLE RECORDING MEDIUM FOR IMAGE DATA FROM MULTIPLE VIEWPOINTS

BACKGROUND OF THE INVENTION

1. Field of the Invention

The present invention relates to a medical image processing apparatus and method appropriate for comparison reading of medical images of an examined subject (patient), and a computer-readable recording having stored therein a program for causing a computer to execute the medical image processing method.

2. Description of the Related Art

In recent years, modalities using various techniques, such as an X-ray CT (Computed Tomography) apparatus, an ultrasonic (US) diagnosis apparatus, an MRI (Magnetic Resonance Imaging) apparatus, a PET (Positron Emission Tomography) apparatus and a SPET (Single-Photon Emission Tomography) apparatus, were used in medical image fields in addition to an X-ray radiography apparatus. As the speed of the modalities became higher, and the performance of the modalities improved to cope with multi-slice tomography or the like, it became possible to perform radiography on a plurality of regions of a patient in a series of operations. Accordingly, it is possible to obtain several hundred to several thousand highly-precise tomographic images of the patient. Further, a plurality of modalities came to be used to obtain medical images for a single candidate disease. Further, in diagnosis using images (image diagnosis), medical images obtained in past radiography are referred to in some cases. Therefore, comparison image reading became often performed. In comparison image reading, medical images obtained by a plurality of modalities and past medical images are compared with each other to make a diagnosis for one candidate disease. Hence, integrated diagnosis became possible.

In comparison image reading as described above, especially when the medical images are tomographic images, it is necessary to match the slice positions of the tomographic images obtained in different series of radiography, which were performed at different time from each other, and to display images of the same slice position. However, since several hundred to several thousand medical images are obtained in a series of radiography, the operation for matching the slice positions of slice images to be compared with each other imposes an extremely heavy burden on users.

Therefore, a method for automatically displaying images of the anatomically same slice position is proposed (please refer to Japanese Unexamined Patent Publication No. 2001-137230 (Patent Document 1)). In the method, a region of a specific organ, such as the lung field, heart and descending aorta, is extracted from a present medical image, which is a target of image reading, and a past medical image. Further, anatomical positions with respect to the body axis direction of a patient are matched between the present medical image and the past medical image based on an index with respect to the size and the morphology of the region extracted from the present medical image and the region extracted from the past medical image. Accordingly, images of the anatomically same slice position are automatically displayed. When the method disclosed in Patent Document 1 is used, an operation for matching the slice positions is not necessary. Therefore, it is possible reduce the burden on users in comparison image reading.

When image diagnosis is made in an actual field of medicine, diagnosis is often made by cooperation of a doctor in each clinical department, who requests image reading or diagnosis, (hereinafter, referred to as a requesting doctor) and a doctor or radiologist who is specialized in image reading (hereinafter, referred to as an image reading doctor). Specifically, after a radiographer obtains a medical image of a patient by performing radiography on the patient based on an examination order from the requesting doctor, the image reading doctor performs image reading on the medical image. The image reading doctor prepares an image reading report summarizing the result of image reading, and sends the image reading report to the requesting doctor. The requesting doctor reads a finding included in the image reading report. The requesting doctor makes a final diagnosis by referring to an image attached to the image reading report while taking various kinds of information, such as the result of questioning the patient and other examination results, into consideration.

As a conventional technique related to preparation of the image reading report and reference to the image reading report, a medical report preparation/reference apparatus is known (please refer to U.S. Patent Application Publication No. 20050226405 (Patent Document 2)). In the apparatus, when the image reading report is prepared, links are generated, based on an input operation by a user, in key character strings in the finding. The links are generated to clearly show correspondence between each of a plurality of images attached to the image reading report and a part of the content of the finding in the image reading report related to the respective images. The key character strings are linked to addresses of medical images that should be referred to together with the key character strings. Further, the key character strings are linked to image edit parameter, such as a window level, a window width and a magnification ratio. When the image reading report is referred to, if a person who views the image reading report clicks a character string in which a link is generated, a medical image linked to the character string is edited based on the image edit parameter, and displayed.

Further, a virtual endoscope technique is known. In the virtual endoscope technique, an image similar to an image obtained by using an endoscope is generated from a tomographic image obtained by radiography using a CT apparatus or the like. This technique is commonly used in North America especially in detection of tumors in large intestines, because tumors are detected only by CT radiography without examination using an endoscope. Further, a technique using the virtual endoscopic image has been proposed to perform safe and speedy surgery, examination or the like by using an endoscope.

For example, Japanese Unexamined Patent Publication No. 2006-198032 (Patent Document 3) discloses a technique of displaying a virtual endoscopic image of a peripheral region that does not appear in an endoscopic image when observation is performed by using an endoscope. The virtual endoscopic image of the peripheral region is superimposed on an endoscopic image obtained by the endoscope. The technique can assist a doctor in surgery using the endoscope. Further, Japanese Unexamined Patent Publication No. 2000-135215 (Patent Document 4) discloses a technique of generating a virtual endoscopic image of a duct, such as a bronchus. In this technique, the virtual endoscopic image is used to obtain, in advance, the movement path of an endoscope to a target point along the duct. A virtual endoscopic image along the path is used as a guide image when observation is performed actually by using an endoscope. The techniques disclosed in Patent Documents 3 and 4 can perform safe and speedy observation using an endoscope by displaying a virtual endoscopic image together with an endoscopic image.

However, in the method disclosed in Patent Document 1, the slice positions are matched based on the size of a region extracted from the present medical image, which is the target of image reading, and the size of a region extracted from the past medical image. Therefore, the accuracy of matching the positions is not sufficient. Consequently, it is necessary to manually correct the slice positions after the medical images are displayed. Further, in the method disclosed in Patent Document 2, a medical image correlated with the image reading report can be displayed by referring to the image reading report. However, in comparison image reading, a word that is correlated with a medical image to be compared with needs to be found in the image reading report. Therefore, the operation for searching the image reading report for the word is extremely troublesome. Further, when the medial image to be compared with is not correlated with any word in the image reading report, it is impossible to display the medical image.

SUMMARY OF THE INVENTION

In view of the foregoing circumstances, it is an object of the present invention to make it possible to accurately identify a medical image of the same viewpoint position, such as the same slice position.

A first medical image processing apparatus of the present invention is a medical image processing apparatus comprising:

a target viewpoint position determination means that determines a target viewpoint position in a first medical image having multiple viewpoints;

a first information obtainment means that obtains, as first information, information about an anatomical structure and/or a lesion in the first medical image from the first medical image;

a second information obtainment means that obtains, as second information, information about an anatomical structure and/or a lesion in a finding with respect to at least one second medical image of the same examined person as the first medical image, the information being related to the first information, from image reading report information including the finding, each of the at least one second medical image having multiple viewpoints and having been obtained at different time from obtainment of the first medical image, the image reading report information being correlated with an image of a viewpoint position at which the finding was prepared; and an image determination means that determines, based on the viewpoint position of the image correlated with the image reading report information from which the second information has been obtained, an image of a corresponding viewpoint position, which corresponds to the target viewpoint position.

The "medical image having multiple viewpoints" is a medical image that can identify different images for respective viewpoints when a viewing position (in other words, a viewpoint) is changed within the image. For example, in a multi-slice tomographic image obtained by the X-ray CT apparatus, as described above, a slice position may be regarded as the position of a viewpoint for observation, and images of different slice positions are identified by changing the slice positions. Therefore, the multi-slice tomographic image may be used as the medical image having multiple viewpoints. Further, in a virtual endoscope technique, which uses a virtual endoscopic image generated from a multi-slice tomographic image, a virtual endoscopic image of a different position can be identified by changing the position of a desired viewpoint. Further, in a real endoscopic image, which is obtained by actually inserting an endoscope into the body cavity of a patient to image the body cavity, a motion image or a still image of the real endoscopic image at a desired viewpoint can be identified by changing the position of the desired viewpoint in the body cavity. Therefore, the virtual endoscopic image and the real endoscopic image may be used as the medical images having multiple viewpoints.

Further, in the first medical image processing apparatus of the present invention, the first information obtainment means may obtain the first information from an image of the target viewpoint position in the first medical image.

A second medical image processing apparatus of the present invention is a medical image processing apparatus comprising:

a target viewpoint position determination means that determines a target viewpoint position in a first medical image having multiple viewpoints;

a first information obtainment means that obtains, as first information, information about an anatomical structure and/or a lesion in a finding with respect to an image of the target viewpoint position from image reading report information including the finding;

a second information obtainment means that obtains, as second information, information about an anatomical structure and/or a lesion in a finding with respect to at least one second medical image of the same examined person as the first medical image, the information being related to the first information, from image reading report information including the finding, each of the at least one second medical image having multiple viewpoints and having been obtained at different time from obtainment of the first medical image, the image reading report information being correlated with an image of a viewpoint position at which the finding was prepared; and an image determination means that determines, based on the viewpoint position of the image correlated with the image reading report information from which the second information has been obtained, an image of a corresponding viewpoint position, which corresponds to the target viewpoint position.

The "anatomical structure" may be structures in various levels, such as a radiographed or imaged region, an internal organ, an organ, a part of the internal organ or organ and a tissue. Specific examples of the anatomical structure are the head, the chest and the like as the radiographed region, the brain, lung, liver and the like as the internal organ or the like, the frontal lobe, left lung, upper lobe (superior lobe) of left lung, liver segment and the like as a part of an internal organ or the like, a bone, blood vessel and the like as an organ, the fifth lumbar vertebra and hepatic artery as specific bones or blood vessels, and the like.

The "lesion" is a lesion in the anatomical structure. Specific examples of the lesion are a node, a diffuse disease, a tumor, a stricture, an infarct, and the like.

Therefore, in the present invention, the "information about an anatomical structure and/or a lesion" may be defined as the anatomical structure per se and/or the lesion per se.

The information about the anatomical structure and/or the lesion may be obtained from the image reading report information, for example, by preparing keywords representing the anatomical structure and/or the lesion in advance, and by extracting the keywords from the image reading report information. Alternatively, the information about the anatomical structure and/or the like may be obtained by known language analysis.

The first and second medical image processing apparatuses of the present invention may further include a display control means that displays a display screen (what is displayed on a display monitor screen) including an image of the target viewpoint position (an image viewed at the target viewpoint position) and an image of the corresponding viewpoint position (an image viewed at the corresponding viewpoint position) on a display means.

In the first and second medical image processing apparatuses of the present invention, when the number of images of the corresponding viewpoint position is one, the display control means may display the display screen including the image of the corresponding viewpoint position on the display means.

In the first and second medical image processing apparatuses of the present invention, when the number of images of the corresponding viewpoint position is at least two (in other words, two or greater), the display control means may display the display screen including a list of information for identifying the at least two images of the corresponding viewpoint position on the display means, and further display, on the display means, an image of a corresponding viewpoint position identified in the list.

In the first and second medical image processing apparatuses of the present invention, when the number of images of the corresponding viewpoint position is at least two, the display control means may display the display screen including all images of the corresponding viewpoint position on the display means.

In the first and second medical image processing apparatuses of the present invention, when the number of images of the corresponding viewpoint position is at least two, the display control means may display the display screen in which all images of the corresponding viewpoint position are switchable on the display means.

In the first and second medical image processing apparatuses of the present invention, the display control means may display the display screen on the display means in such a manner that a most-recently-obtained image of the corresponding viewpoint position is in a selected state.

In the first and second medical image processing apparatuses of the present invention, the display control means may display the display screen including the date/time (date, date and time, or the like) of obtainment of each of all the images of the corresponding viewpoint position on the display means.

In the first and second medical image processing apparatuses of the present invention, the image determination means may identify the viewpoint position of the image correlated with the image reading report information from which the second information has been obtained, and determine the image of the corresponding viewpoint position based on a correlation between an image of a viewpoint position in a predetermined range with respect to the identified viewpoint position and the image of the target viewpoint position.

In the first and second medical image processing apparatuses of the present invention, the first medical image having multiple viewpoints maybe a multi-slice tomographic image, and the at least one second medical image each having multiple viewpoints may be a multi-slice tomographic image.

In the first and second medical image processing apparatuses of the present invention, the first medical image having multiple viewpoints may be a virtual endoscopic image generated from a multi-slice tomographic image, and the at least one second medical image each having multiple viewpoints maybe a real endoscopic image or a multi-slice tomographic image.

A first medical image processing method of the present invention is a medical image processing method comprising the steps of:

determining a target viewpoint position in a first medical image having multiple viewpoints by using a processing apparatus;

obtaining, as first information, information about an anatomical structure and/or a lesion in the first medical image from the first medical image;

obtaining, as second information, information about an anatomical structure and/or a lesion in a finding with respect to at least one second medical image of the same examined person as the first medical image, the information being related to the first information, from image reading report information including the finding, each of the at least one second medical image having multiple viewpoints and having been obtained at different time from obtainment of the first medical image, the image reading report information being correlated with an image of a viewpoint position at which the finding was prepared; and determining, based on the viewpoint position of the image correlated with the image reading report information from which the second information has been obtained, an image of a corresponding viewpoint position, which corresponds to the target viewpoint position.

A second medical image processing method of the present invention is a medical image processing method comprising the steps of:

determining a target viewpoint position in a first medical image having multiple viewpoints by using a processing apparatus;

obtaining, as first information, information about an anatomical structure and/or a lesion in a finding with respect to an image of the target viewpoint position from image reading report information including the finding;

obtaining, as second information, information about an anatomical structure and/or a lesion in a finding with respect to at least one second medical image of the same examined person as the first medical image, the information being related to the first information, from image reading report information including the finding, each of the at least one second medical image having multiple viewpoints and having been obtained at different time from obtainment of the first medical image, the image reading report information being correlated with an image of a viewpoint position at which the finding was prepared; and determining, based on the viewpoint position of the image correlated with the image reading report information from which the second information has been obtained, an image of a corresponding viewpoint position, which corresponds to the target viewpoint position.

A third medical image processing apparatus of the present invention is a medical image processing apparatus comprising:

a target slice position determination means that determines a target slice position in a first tomographic image having multi-slice planes;

a first information obtainment means that obtains, as first information, information about an anatomical structure and/or a lesion in the first tomographic image from the first tomographic image;

a second information obtainment means that obtains, as second information, information about an anatomical structure and/or a lesion in a finding with respect to at least one second tomographic image of the same examined person as the first tomographic image, the information being related to the first information, from image reading report information including the finding, each of the at least one second tomographic image having multi-slice planes and having been obtained at different time from obtainment of the first tomographic image, the image reading report information being correlated with an image of a slice position at which the finding was prepared; and an image determination means that determines, based on the slice position of the image correlated with the image reading report information from which the second information has been obtained, an image of a corresponding slice position, which corresponds to the target slice position.

A fourth medical image processing apparatus of the present invention is a medical image processing apparatus comprising:

a target slice position determination means that determines a target slice position in a first tomographic image having multi-slice planes;

a first information obtainment means that obtains, as first information, information about an anatomical structure and/or a lesion in a finding with respect to an image of the target slice position from image reading report information including the finding;

a second information obtainment means that obtains, as second information, information about an anatomical structure and/or a lesion in a finding with respect to at least one second tomographic image of the same examined person as the first tomographic image, the information being related to the first information, from image reading report information including the finding, each of the at least one second tomographic image having multi-slice planes and having been obtained at different time from obtainment of the first tomographic image, the image reading report information being correlated with an image of a slice position at which the finding was prepared; and an image determination means that determines, based on the slice position of the image correlated with the image reading report information from which the second information has been obtained, an image of a corresponding slice position, which corresponds to the target slice position.

A third medical image processing method of the present invention is a medical image processing method comprising the steps of:

determining a target slice position in a first tomographic image having multi-slice planes by using a processing apparatus;

obtaining, as first information, information about an anatomical structure and/or a lesion in the first tomographic image from the first tomographic image;

obtaining, as second information, information about an anatomical structure and/or a lesion in a finding with respect to at least one second tomographic image of the same examined person as the first tomographic image, the information being related to the first information, from image reading report information including the finding, each of the at least one second tomographic image having multi-slice planes and having been obtained at different time from obtainment of the first tomographic image, the image reading report information being correlated with an image of a slice position at which the finding was prepared; and determining, based on the slice position of the image correlated with the image reading report information from which the second information has been obtained, an image of a corresponding slice position, which corresponds to the target slice position.

A fourth medical image processing apparatus of the present invention is a medical image processing apparatus comprising:

determining a target slice position in a first tomographic image having multi-slice planes by using a processing apparatus;

obtaining, as first information, information about an anatomical structure and/or a lesion in a finding with respect to an image of the target slice position from image reading report information including the finding;

obtaining, as second information, information about an anatomical structure and/or a lesion in a finding with respect to at least one second tomographic image of the same examined person as the first tomographic image, the information being related to the first information, from image reading report information including the finding, each of the at least one second tomographic image having multi-slice planes and having been obtained at different time from obtainment of the first tomographic image, the image reading report information being correlated with an image of a slice position at which the finding was prepared; and determining, based on the slice position of the image correlated with the image reading report information from which the second information has been obtained, an image of a corresponding slice position, which corresponds to the target slice position.

The first through fourth medical image processing methods of the present invention may be provided as programs for causing a computer to execute the methods, or as computer-readable recording media having stored therein the programs.

According to the present invention, information about an anatomical structure and/or a lesion in a first medical image is obtained as first information. Then, information about an anatomical structure and/or a lesion in a finding with respect to at least one second medical image of the same examined person as the first medical image, the information being related to the first information, is obtained, as second information, from image reading report information. The image reading report information includes the finding, and each of the at least one second medical image has multiple viewpoints and was obtained at different time from obtainment of the first medical image. Further, the image reading report information is correlated with an image of a slice position at which the finding was prepared. The image correlated with the image reading report information from which the second information has been obtained is determined as an image of a corresponding slice position, which corresponds to the target slice position. Therefore, compared with the method of identifying a slice position by image processing, as described in Patent Document 1, it is possible to accurately identify slice images of the same slice position in the first medical image and the second medical image (images).

Further, it is possible to reduce processing time for obtaining the first information, especially, by obtaining the first information from an image of the target viewpoint position in the first medical image.

Further, a display screen including the image of the target viewpoint position and the image of the corresponding viewpoint position is displayed. Therefore, the viewpoint positions of the images included in the display screen are the same. Hence, accurate comparison image reading is possible.

Further, when the number of images of the corresponding viewpoint position is at least two, if a display screen including a list of information for identifying the at least two images of the corresponding viewpoint position is displayed, and further an image of a corresponding viewpoint position identified in the list is displayed, it is possible to display an image of a desired corresponding viewpoint position.

Further, when the number of images of the corresponding viewpoint position is at least two, if a display screen including all images of the corresponding viewpoint position, or a display screen in which all images of the corresponding viewpoint position are switchable is displayed, it is possible to easily compare the plurality of images of the corresponding viewpoint position and the image of the target viewpoint position.

In this case, if a display screen is displayed in such a manner that a most-recently-obtained image of the corresponding viewpoint position is in a selected state, it is possible to easily compare the first medical image and the most-recently-obtained second medical image.

Further, it is possible to easily recognize the date/time of obtainment of the second medical image by displaying a display screen including the date/time of obtainment of each of all the images of the corresponding viewpoint position. Consequently, it is possible to easily perform comparison image reading on the first medical image and the second medical image obtained at a desired date/time of obtainment.

Further, it is possible to accurately match the viewpoint position in the first medical image and the viewpoint position in the second medical image by identifying the viewpoint position of the image correlated with the image reading report information from which the second information has been obtained, and by determining the image of the corresponding viewpoint position based on a correlation between an image of a viewpoint position in a predetermined range in the vicinity of the identified viewpoint position and the image of the target viewpoint position.

Note that the program of the present invention may be provided being recorded on a computer readable medium. Those who are skilled in the art would know that computer readable media are not limited to any specific type of device, and include, but are not limited to: floppy disks, CD's RAM'S, ROM's, hard disks, magnetic tapes, and internet downloads, in which computer instructions can be stored and/or transmitted. Transmission of the computer instructions through a network or through wireless transmission means is also within the scope of this invention. Additionally, computer instructions include, but are not limited to: source, object and executable code, and can be in any language including higher level languages, assembly language, and machine language.

BRIEF DESCRIPTION OF THE DRAWINGS

FIG. 9 is a diagram illustrating an example of a display screen for comparison image reading (No. 1);

FIG. 10 is a diagram illustrating an example of a display screen for comparison image reading (No. 2);

DESCRIPTION OF THE PREFERRED EMBODIMENTS

Figure 1:
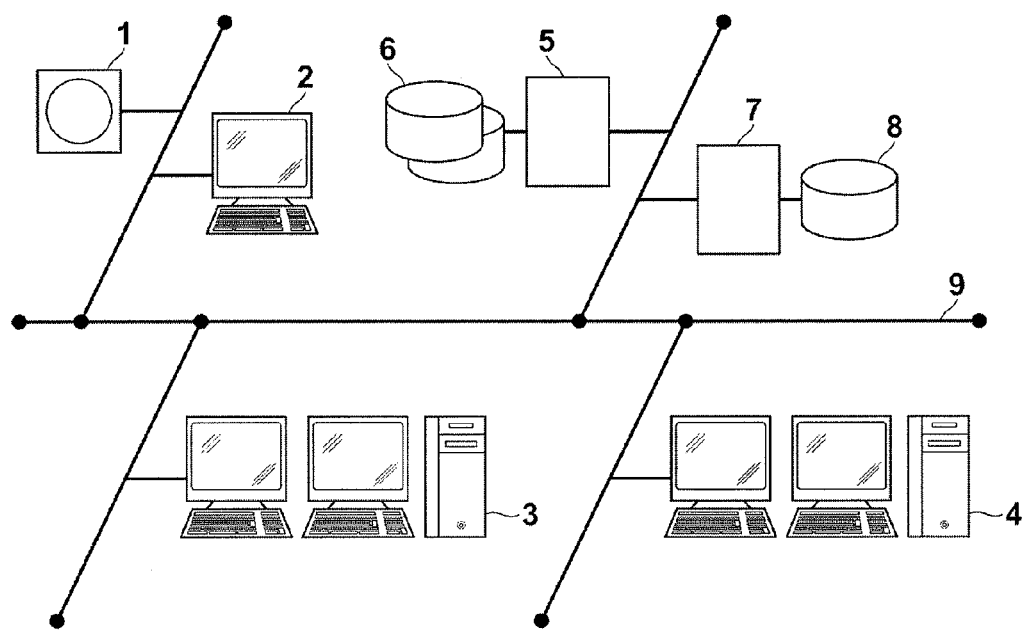
FIG. 1 is a schematic diagram illustrating the configuration of a medical information system to which a medical image processing apparatus according to a first embodiment of the present invention has been applied.

Hereinafter, embodiments of the present invention will be described with reference to drawings. FIG. 1 is a schematic diagram illustrating the configuration of a medical information system to which a medical image processing apparatus according to a first embodiment of the present invention has been applied. The system is used to perform radiography on a region to be examined of a subject (patient) based on an examination order given by a doctor in a clinical department by using a known ordering system, and to store data or images obtained by radiography. Further, the system is used by a radiologist or doctor in a radiology department, who is specialized in image reading, to read images and to prepare a report on the result of image reading. Further, the system is used by the doctor in the clinical department who requested radiography. The doctor in the clinical department uses the system to view (retrieve) the report on the result of image reading and to observe, in detail, an image on which image reading was performed by the radiologist. As illustrated in FIG. 1, a radiography apparatus (modality) 1 for medical images, a workstation (QA-WS) 2 for checking image quality, a workstation 3 for a radiology department, a workstation 4 for a clinical department, an image information management server 5, an image information database 6, an image reading report server 7, and an image reading report database 8 are connected to each other through a network 9 in such a manner that they can communicate with each other. Each unit or device is controlled by a program installed therein from a recording medium, such as a CD-ROM. Alternatively, the program may be downloaded from a recording device of a server connected to the unit or device through a network, such as the Internet, and installed in the unit or device.

The modality 1 may be an apparatus that generates image data representing an image of a region of a subject to be examined by performing radiography on the region of the subject. The apparatus may output, as image information, the image data by attaching supplementary information defined by DICOM standard to the image data. Specific examples of the modality 1 are a CT (computed tomography), an MRI (magnetic resonance imaging), a PET (positron emission tomography), an ultrasonic imaging apparatus, an X-ray radiographic apparatus using a flat panel X-ray detector (FPD), and the like. Hereinafter, a pair of image data representing a subject and supplementary information to the image data will be referred to as "image information." In other words, the "image information" may include text information related to the image.

The workstation (QA-WS) 2 for checking image quality includes a general-purpose processing apparatus (computer), one or two high resolution displays (display screen monitors), and an input device, such as a keyboard or a mouse. Further, software for assisting a radiographer or an examination technician in his/her work is installed in the processing apparatus. The QA-WS 2 receives image information in accordance with DICOM from the modality 1 by a function realized by executing the software program thereof. Further, the QA-WS 2 displays, on a display or displays, image data and the content of supplementary information included in the received image information so that the radiographer or the examination technician checks the image information. After the radiographer or the examination technician checks the image information, the image information is transferred to the image information management server 5 through the network 9. Further, registration of the image information in the image information database 6 is requested.

The workstation 3 for a radiology department is a computer used by a doctor or radiologist in the radiology department who is specialized in image reading in the radiology department. The workstation 3 for the radiology department is used to perform image reading and to prepare a report on image reading. The workstation 3 for the radiology department has known hardware configuration, such as a CPU (central processing unit), a main storage device, an auxiliary storage device, an input/output interface, a communication interface, an input device, a display device, and a data bus. Further, a known operation system or the like is installed in the workstation 3 for the radiology department. The workstation 3 for the radiology department includes a display device and one or two high resolution displays. The device is used to request retrieval of an image from the image information management server 5 to view the image. Further, the device is used to display an image received from the image information management server 5. The device is used to perform automatic detection of a suspected lesion region in the image, and to display the detected suspected lesion region in an emphasized manner. Further, the device assists a radiologist in preparing an image reading report. The device is used to request registration of the image reading report in the image reading report server 7, and to request retrieval of the image reading report from the image reading report server 7 to view the image reading report. Further, the device is used to display the image reading report received from the image reading report server 7. Each processing is performed by executing respective software programs.

The workstation 4 for a clinical department is a computer that is used by a doctor in the clinical department to observe an image in detail and to view an image reading report. Further, the workstation 4 for the clinical department is used by the doctor in the clinical department to view an electronic chart (or clinical record) and to input data to the electric chart. The workstation 4 for the clinical department has known hardware configuration, such as a CPU, a main storage device, an auxiliary storage device, an input/output interface, a communication interface, an input device, a display device, and a data bus. Further, a known operation system or the like is installed in the workstation 4 for the clinical department. The workstation 4 for the clinical department includes a display device and one or two high resolution displays. The device is used to request retrieval of an image from the image information management server 5 to view the image. Further, the device is used to display the image received from the image information management server 5. Further, the device is used to perform automatic detection of a suspected lesion region in the image, and to display the detected suspected lesion region in an emphasized manner. Further, the device is used to request retrieval of the image reading report from the image reading report server 7 to view the image reading report. Further, the device is used to display the image reading report received from the image reading report server 7. Each processing is performed by executing respective software programs. The medical image processing apparatus of the present invention is installed in the workstation 4 for the clinical department, as described later.

The image information management server 5 is a general-purpose computer having relatively-high processing performance in which a software program that provides a function of a database management system (DataBase Management System: DBMS) is installed. The image information management server 5 includes a large capacity storage device in which the image information database 6 is configured. The storage device may be a large capacity hard disk device that is connected to the image information management server 5 through a data bus. Alternatively, the storage device may be an NAS (Network Attached Storage) connected to the network 9 or a disk device connected to an SAN (Storage Area Network).

In the image information database 6, image data representing an image of a subject and supplementary information to the image data are registered. The supplementary information may include, for example, an image ID for identifying (distinguishing) an individual image, a patient ID for identifying a subject (patient), an examination ID for identifying an examination, a unique ID (UID) allocated to each image information, an examination date on which the image information was generated, time of examination, the kind of a modality used in the examination for obtaining the image information, patient information, such as the name, age and sex of the patient, an examined region (radiographed region), radiography conditions (use or non-use of contrast agent, the dose of radiation, and the like), and the like. Further, the supplementary information may include information, such as a series number or an acquisition number, when a plurality of images are obtained in one examination or radiography. The image information may be managed, for example, as XML data or SGML data.

When the image information management server 5 receives a request for registration of image information from the QA-WS 2, the image information management server 5 registers the image information in the image information database 6 in accordance with the format of the database.

When the image information management server 5 receives a viewing (retrieval) request that has been sent from the workstation 3 for the radiology department or the workstation 4 for the clinical department through the network 9, the image information management server 5 searches the image information database 6 for the image information registered in the image information database 6 to extract the image information. The image information management server 5 sends the extracted image information to the workstation 3 for the radiology department or the workstation 4 for the clinical department that has requested the image information.

When a user, such as a radiologist who performs image diagnosis (reading) or a doctor in a clinical department, performs an operation for requesting retrieval of an image to be read or observed, the workstation 3 for the radiology department or the workstation 4 for the clinical department sends a retrieval request to the image information management server 5, and obtains necessary image information. The obtained image information is displayed on a monitor screen, and processing, such as automatic detection of a lesion, is performed by a request by the user.

On a monitor of the workstation 3 for the radiology department displays, a report preparation display screen that assists the radiologist in preparation of an image reading report is displayed. When the radiologist inputs text representing the content of his/her finding based on image reading and the like, an image reading report is generated. The image reading report records the information that has been input by the radiologist and an image that was observed in image reading (hereinafter, referred to as image reading target image). When the number of the image reading target images is two or greater, the image reading report records a representative image that most clearly represents the finding in image reading (hereinafter, referred to as a representative image). The workstation 3 for the radiology department transfers the generated image reading report to the image reading report server 7 through the network 9. Further, the workstation 3 for the radiology department requests registration of the image reading report in the image reading report database 8.

The image reading report server 7 is a general-purpose computer having relatively-high processing performance in which a software program that provides a function of a database management system (DataBase management System: DBMS) is installed. When the image reading report server 7 receives a request for registration of an image reading report from the workstation 3 for the radiology department, the image reading report server 7 registers the image reading report in the image reading report database 8 in accordance with the format of the database.

The image reading report database 8 registers, for example, an image ID for identifying an image reading target image or a representative image, an image-reader ID for identifying a radiologist who performed image reading, position information about a region of interest, a finding and information, such as the degree of confidence or certainty in the finding. Further, the image reading report database 8 may register an examination number or a patient number that was obtained by referring to supplementary information attached to image information during image reading. Further, the image reading report database 8 may register image data itself that represents the image reading target image or the representative image. The image data representing the image reading target image or the representative image maybe registered as reduced image data (thinned image data) having a smaller number of pixels than the image data registered in the image information database 6. In the present embodiment, link information (an address, a folder name, a file name or the like of image data registered in the image information database 6) is also registered in the image reading report database 8. The link information makes it possible to access image data registered in the image information database 6, from which the reduced image data is generated. Alternatively, the image data registered in the image information database 6 may be copied, and registered in the image reading report database 8 without reducing. Further, the position information about the region of interest may be registered, as supplementary information to image data, in the image information database 6 instead of the image reading report database 8. Further, the image reading report may be managed, for example, as XML or SGML data.

When the image reading report server 7 receives a retrieval request that is sent from the workstation 3 for the radiology department or the workstation 4 for the clinical department through the network 9, the image reading report server 7 searches the image reading report database 8 for an image reading report registered in the image reading report database 8 to extract the image reading report, and sends the extracted image reading report to the workstation 3 for the radiology department or the workstation 4 for the clinical department that has originated the request.

The network 9 is a local area network to which various devices within a hospital are connected. When the workstation 3 for the radiology department or the workstation 4 for the clinical department is installed in another hospital or clinic, the network 9 may be configured by connecting local area networks of respective hospitals to each other through the Internet or a dedicated communication line. In either case, it is desirable that the network 9 is an optical network or the like, which can transfer image information at high speed.

Figure 2:
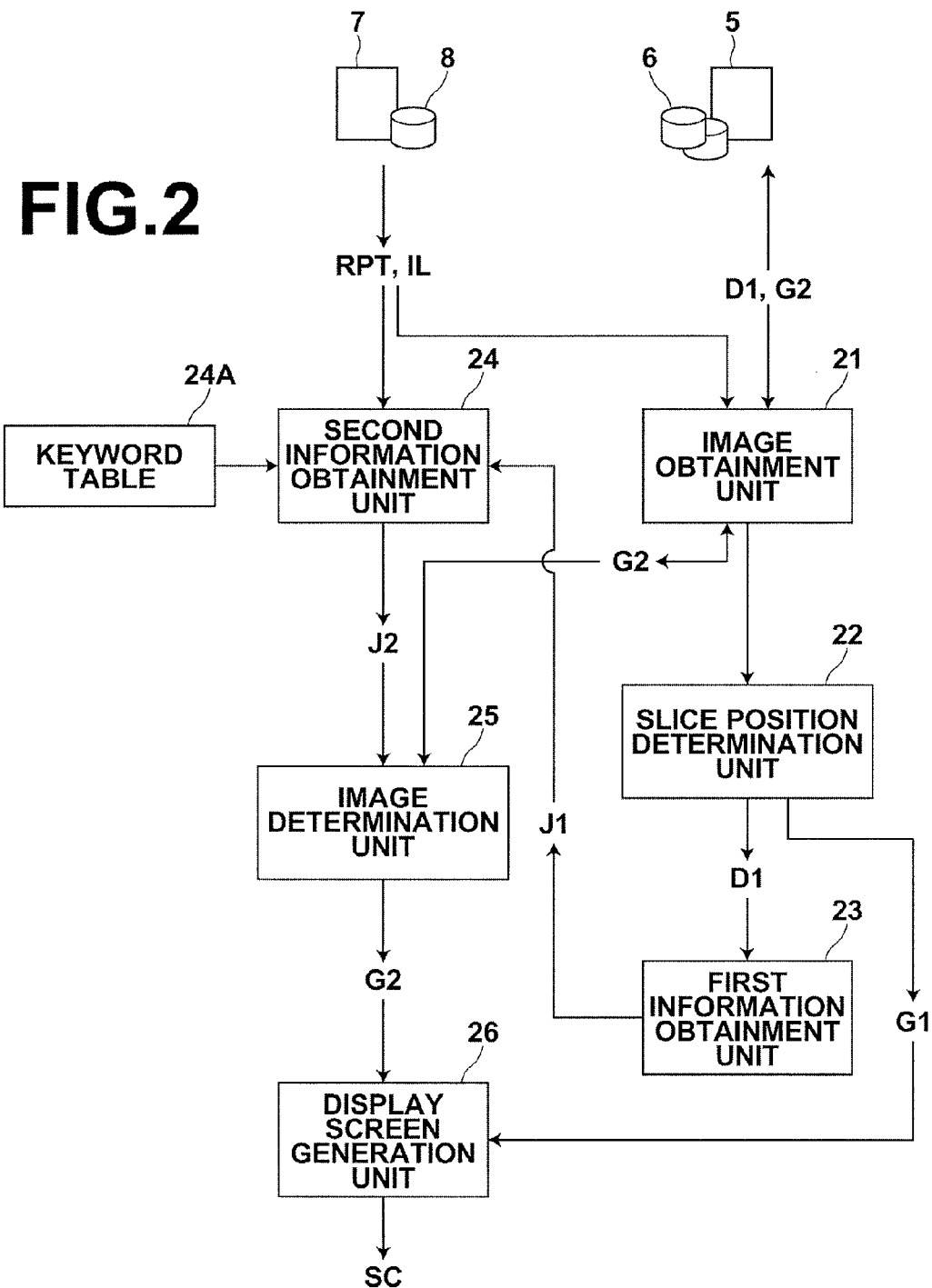
FIG. 2 is a schematic block diagram illustrating the configuration of a medical image display apparatus to which the medical image processing apparatus according to the first embodiment of the present invention has been applied, and which is installed as an image viewing function in a workstation for a clinical department, and the flow of data in the medical image display apparatus.

FIG. 2 is a schematic block diagram illustrating the configuration of a medical image display apparatus to which the medical image processing apparatus according to the first embodiment of the present invention has been applied, and which is installed as an image viewing function in the workstation 4 for the clinical department, and the flow of data in the medical image display apparatus. As illustrated in FIG. 2, the medical image display apparatus according to the first embodiment includes an image obtainment unit 21, a slice position determination unit 22, a first information obtainment unit 23, a second information obtainment unit 24, an image determination unit 25, and a display screen generation unit 26. In the present embodiment, processing for performing comparison image reading on tomographic images obtained at different time from each other will be described.

Figure 3:
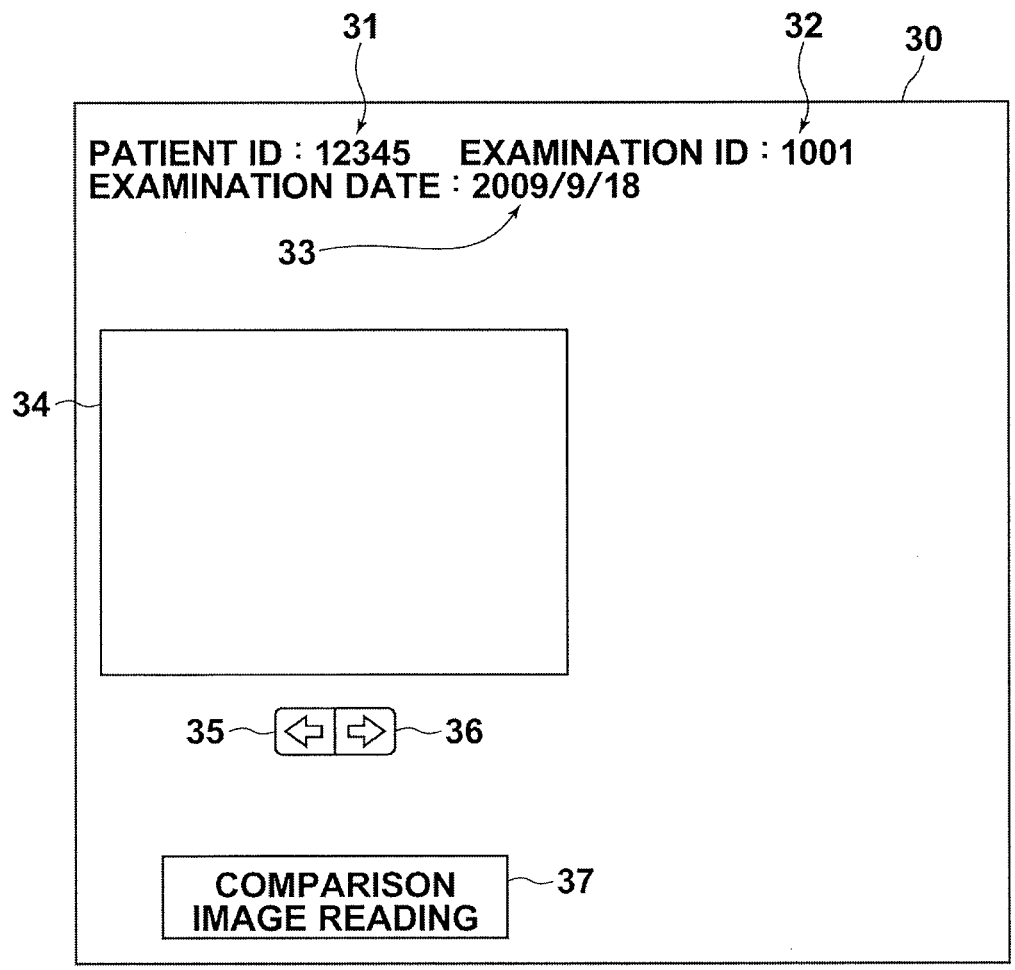
FIG. 3 is a diagram illustrating an example of a start operation in a display screen of an image.

First, a software program for realizing the viewing function is started when a user who is a doctor in a clinical department performs an operation for performing comparison image reading by using a first tomographic image, which is the target of diagnosis (diagnosis target). FIG. 3 is a diagram illustrating an example of a start operation in a display screen of an image. As illustrated in FIG. 3, a display screen 30 of a diagnosis target image includes an area 31 for displaying a patient ID, an area 32 for displaying an examination ID, an area 33 for displaying an examination date, an area 34 for displaying an image at a slice position of an image reading target, switch buttons 35 and 36 for switching slice positions of the image reading target, and a comparison image reading start button 37. Here, it is assumed that first tomographic image D1, which is the target of image reading, has been sent by the image obtainment unit 21 from the image information management server 5 to the workstation 4 of the clinical department. Here, the first tomographic image D1 is a multi-slice image, which includes images at a plurality of slice positions.

The user can switch slice positions of the image reading target in the display screen 30. The user may switch the slice positions by pressing the switch buttons 35 and 36 by a click of a mouse, or by pressing horizontal cursor keys (arrow keys) on the keyboard at the workstation 4 for the clinical department. When the user presses the comparison image reading start button 37 while an image at a slice position of the image reading target, the image including a lesion or the like, is displayed in the area 34, a software program for realizing an image viewing function is started. Alternatively, the software program may be started without displaying the comparison image reading start button 37. In that case, the software program may be started by double clicking an image at a slice position of the image reading target, or the like.

When the software program is started, the slice position determination unit 22 determines, as a target slice position of the image reading target, the slice position of the currently-displayed image. Then, the first image obtainment unit 23 obtains, as first information J1, information about an anatomical structure and/or a lesion from the first tomographic image D1. Here, the information about the anatomical structure in the first information J1 includes at least one of the name of a radiographed region, the name of an internal organ, the name of an organ, the name of a part or a tissue of the internal organ or organ, or synonyms or signs representing the names, or abbreviations of the names, synonyms and the like. Further, the information about the lesion may include the name of the lesion, a synonym or a sign representing the name of the lesion, or an abbreviation of the name, synonym or the like. For example, the name of a radiographed region, such as the head or chest, the name of an internal organ or an organ, such as the brain, lung field, liver, bones, heart or blood vessels, the name of a part of an internal organ or organ, such as the frontal lobe, left lung, right lung, right upper lobe of the lung, or hepatic segment (segment of liver), the name of a specific organ, such as the fifth lumbar vertebra or coronary arteries, or the like may be used as the information about the anatomical structure. Further, the name of a lesion or a symptom, such as an abnormal shadow, calcification, abnormal blood vessels, lung cancer, hepatocellular carcinoma (liver cell carcinoma), hepatic cyst, hepatic hemangioma, bleeding in the liver region, bleeding in the brain region, a node, a tumor, a stricture, an infarct, a diffuse lung disease, such as consolidation, Ground-Glass Opacity (GGO), Crazy-Paving, a honeycomb-like shadow, a pulmonary emphysema shadow and a nodular shadow, or the like, may be used as the information about the lesion.

Here, the first information obtainment unit 23 recognizes a region or an internal organ or organ, or detects a lesion by using a region recognition method disclosed in U.S. Patent Application Publication No. 20080267481, a method for extracting a pulmonary emphysema region disclosed in Japanese Unexamined Patent Publication No. 2007-289335, an extraction method using model fitting disclosed in Japanese Unexamined Patent Publication No. 2007-312837, a method for extracting a region from a medical image disclosed in Japanese Unexamined Patent Publication No. 2002-045807, a method for dividing a region of interest between medical images disclosed in U.S. Pat. No. 7,058,210, or the like. Accordingly, the first information obtainment unit 23 obtains the first information J1. For example, the first information obtainment unit 23 may obtain, as the first information J1, "left lung, node" by recognizing a lung field and by automatically detecting a node. When the first information J1 is obtained, a user may specify, by clicking or the like, a lesion region in an image at a slice position of the image reading target displayed on the display screen 30. Accordingly, even if detection of a lesion fails, at least information about the region can be obtained. Further, the first information J1 may be obtained in such a manner to obtain the information only from image G1 at a target slice position. When the first information J1 is obtained in such a manner, it is possible to reduce processing time, compared with the case of obtaining the first information J1 from images at all slice positions included in the first tomographic image D1.

Figure 4:
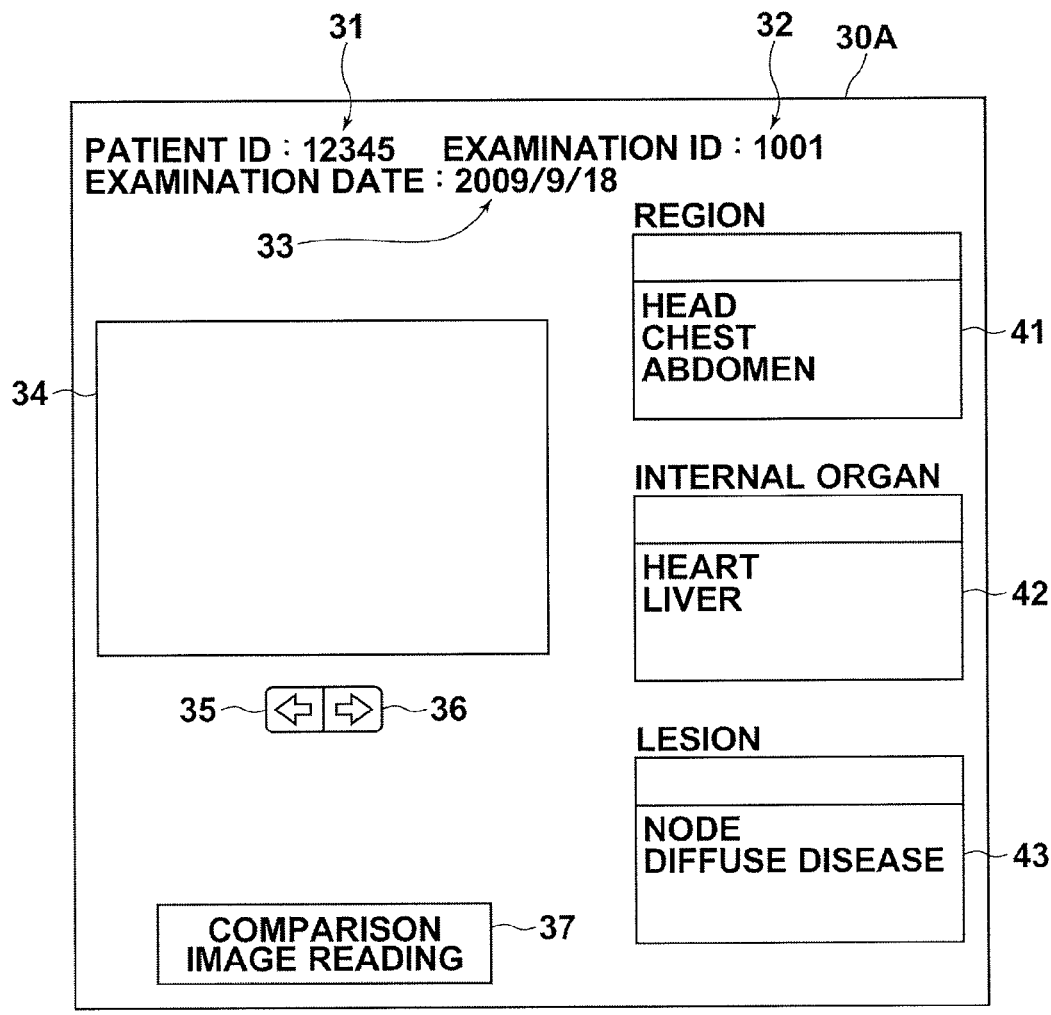
FIG. 4 is a diagram illustrating an example of obtaining first information in a display screen of an image (No. 1)
Figure 5:
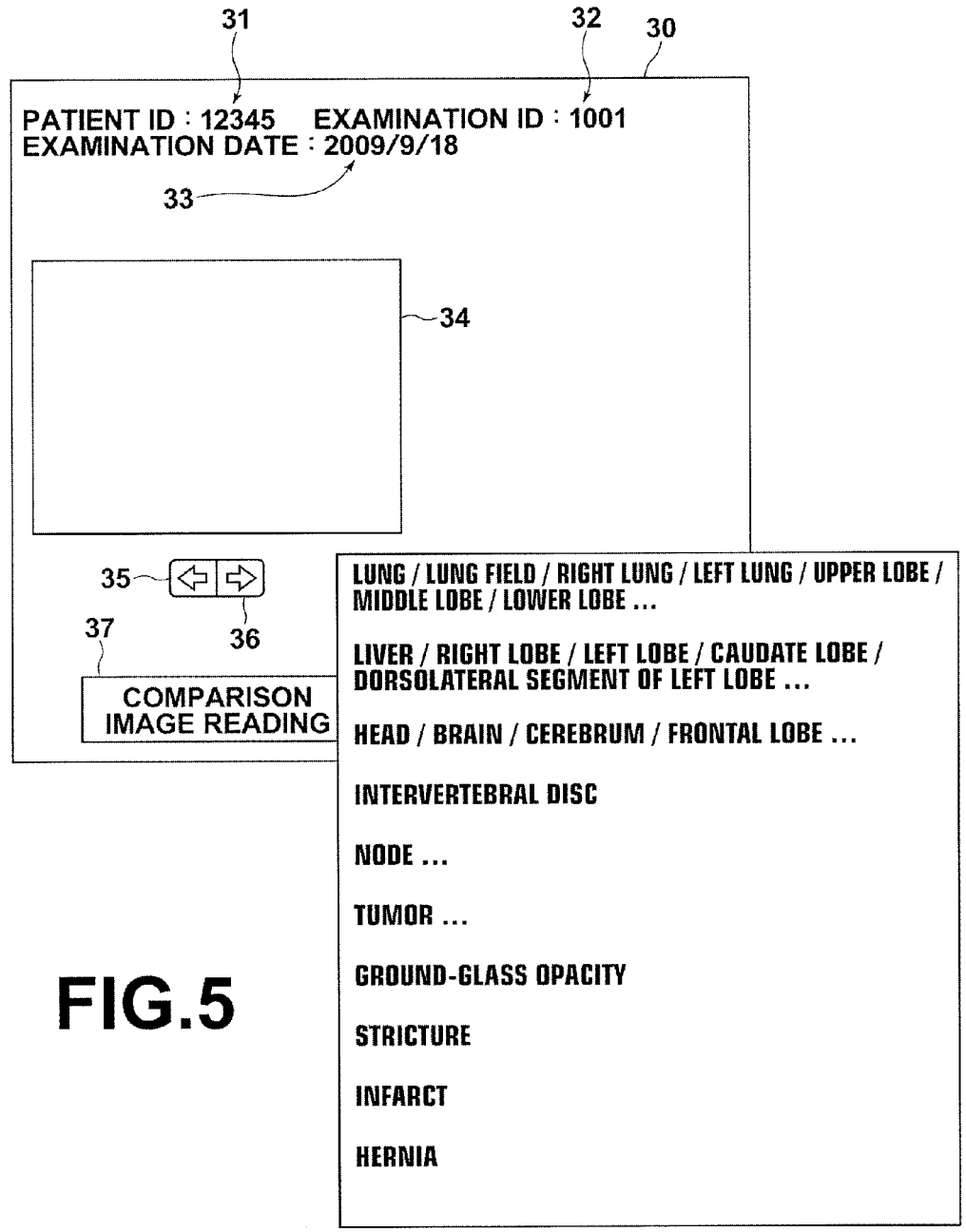
FIG. 5 is a diagram illustrating an example of obtaining first information in a display screen of an image (No. 2)

Further, instead of automatically obtaining the first information J1, the first information obtainment unit 23 may obtain the first information J1 based on an input by the user. In this case, for example, as illustrated in FIG. 4, pulldown menus 41, 42 and 43 may be displayed for a region, the name of an internal organ, a lesion, respectively, in a display screen 30A. Selection of the region, the name of the internal organ and the lesion is input by using the pulldown menus 41, 42 and 43. Alternatively, input of the region, the internal organ, and the lesion in text may be received instead of the input using the pulldown menus. Further, a database may be prepared in advance by extracting keywords from the text of a finding in an image reading report. Further, as illustrated in FIG. 5, keywords obtained from the database may be displayed on a display screen so that the user can select a keyword.

The first information obtainment unit 23 may automatically obtain the first information J1 first. Then, if the first information obtainment unit 23 fails in automatic obtainment of the first information J1, the first information obtainment unit 23 may change the operation so that the first information J1 is obtained based on an input by the user.

Next, the second information obtainment unit 24 accesses the image reading report server 7, and obtains image reading report RPT about a second tomographic image D2 of the same patient as the first tomographic image D1, the second tomographic image D2 being obtained at different time from the time of obtainment of the first tomographic image D1. Further, the second information obtainment unit 24 obtains, as second information J2, an extraction target word related to an anatomical structure and/or a lesion corresponding to the first information J1 from the image reading report RPT.

Figure 6:
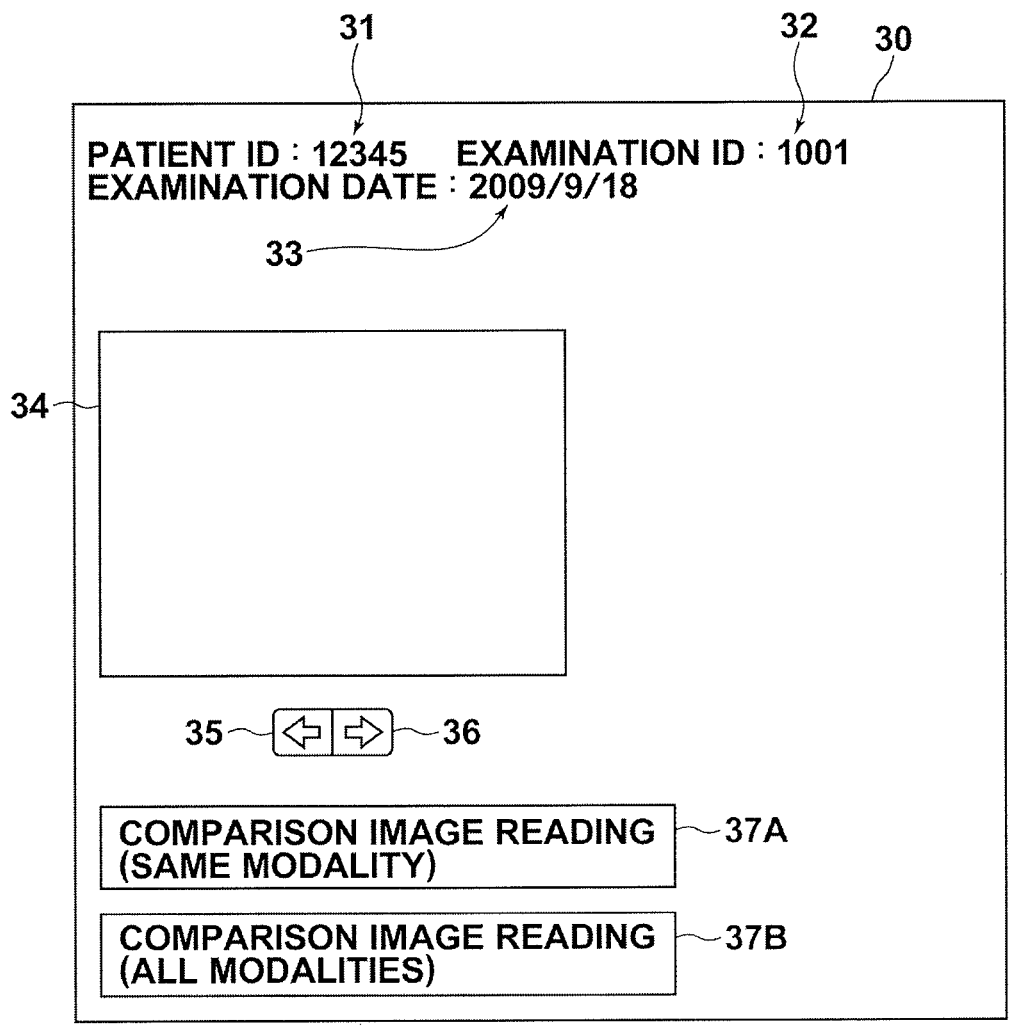
FIG. 6 is a diagram illustrating another example of a start operation in a display screen of an image.

The second tomographic image D2 maybe obtained by using the same modality as the first tomographic image D1 (when the first tomographic image D1 is obtained by a CT apparatus, the second tomographic image D2 is obtained also by the CT apparatus). Alternatively, the second tomographic image D2 may be obtained by using a different modality from the first tomographic image D1 (the second tomographic image D2 is obtained by an apparatus, such as an MRI apparatus, a PET apparatus, an ultrasonic imaging apparatus, a plain or simple X-ray radiography apparatus and an endoscope, other than the CT apparatus). As illustrated in FIG. 6, a "COMPARISON IMAGE READING (SAME MODALITY)" button 37A and a "COMPARISON IMAGE READING (ALL MODALITIES)" button 37B may be displayed in the display screen 30, as comparison image reading start buttons. When the "COMPARISON IMAGE READING (SAME MODALITY)" button 37A is pressed, only an image or images obtained by the same modality are used. When the "COMPARISON IMAGE READING (ALL MODALITIES)" button 37B is pressed, images obtained by all modalities are used. The user may select whether only tomographic images obtained by the same modality should be used, or tomographic images obtained by all modalities should be used.

Figure 7:
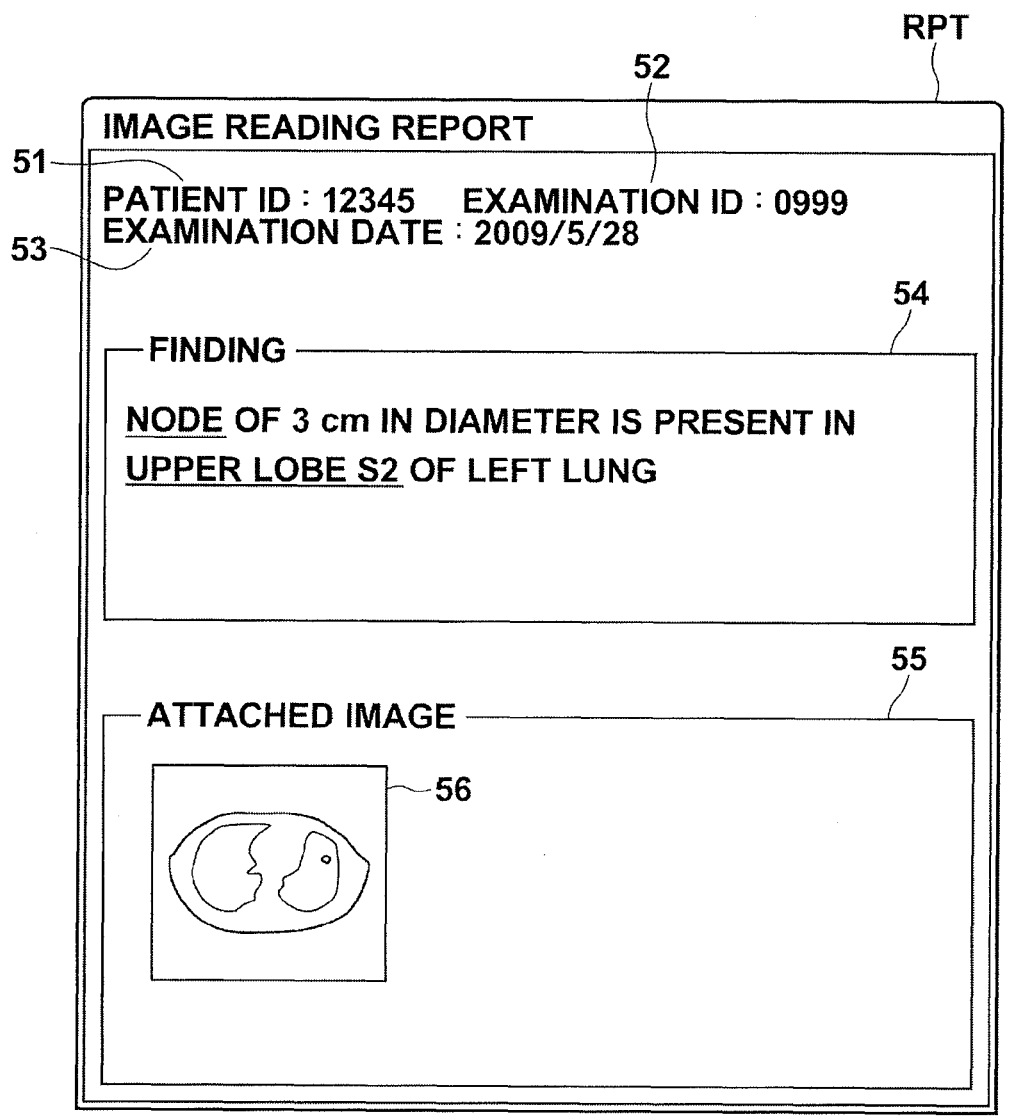
FIG. 7 is a diagram illustrating an example of a display screen of an image reading report.

FIG. 7 is a diagram illustrating an example of a display screen of an image reading report. As illustrated in FIG. 7, the image reading report RPT includes a region 51 for displaying a patient ID, a region 52 for displaying an examination ID, a region 53 for displaying an examination date, a region 54 for displaying a finding with respect to an image reading target image, and an attached image region 55 for displaying a reduced image 56 of an image reading target image or a representative image.

In the image reading report RPT, a link is provided, as described in Patent Document 1. The link correlates a keyword in the finding with an image that should be referred to together with the keyword. For example, as illustrated in FIG. 7, the "upper lobe S2 of left lung" and the "node" are correlated with image data representing images at a slice position at which the reduced image 56 was obtained. Accordingly, when the image reading report RPT is displayed on a display monitor at the workstation 4 for the clinical department, it is possible to display an image at a slice position corresponding to the reduced image 56 by clicking the "upper lobe S2 of left lung" or the "node" in the column of the finding.

Figure 8:
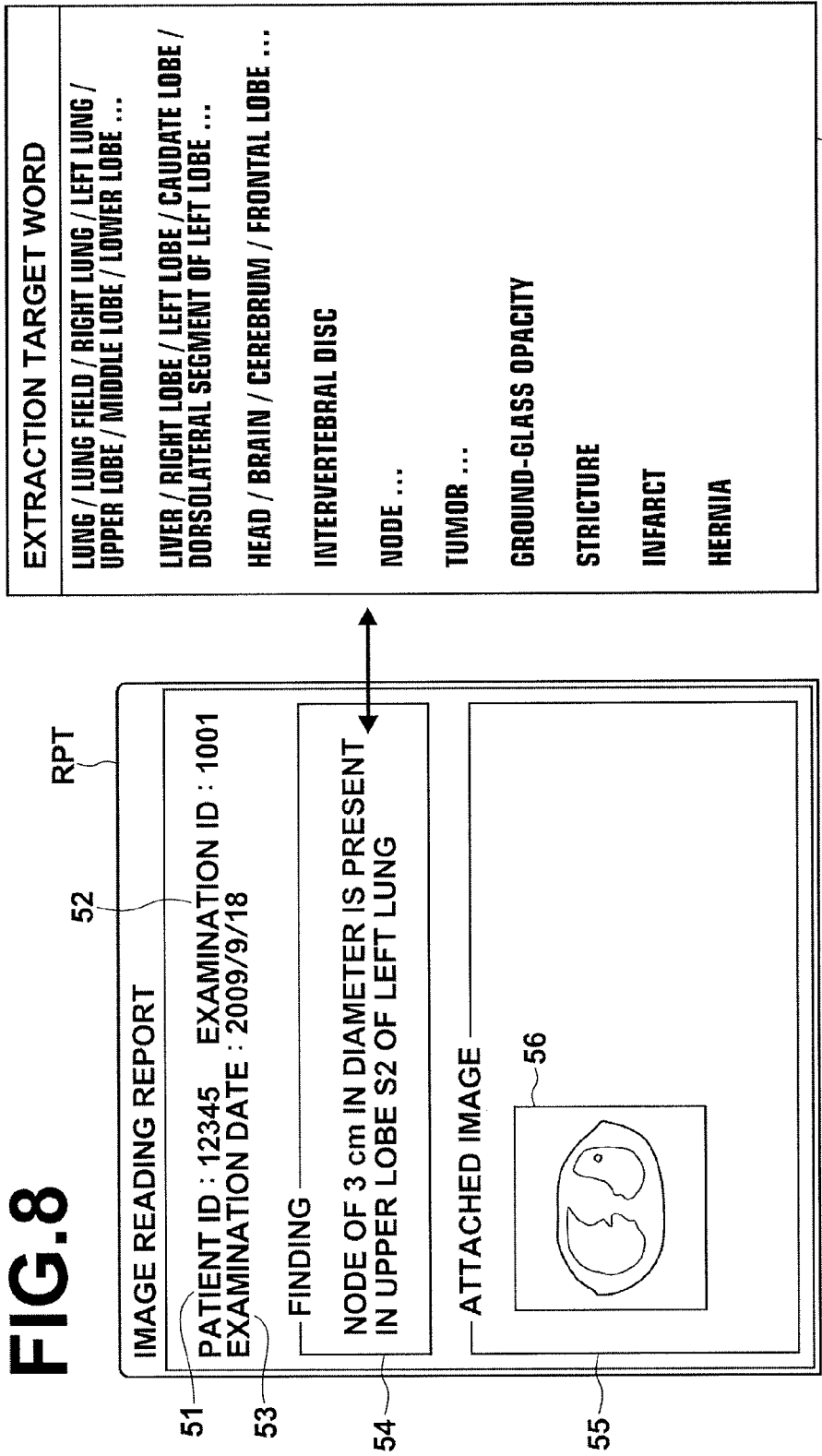
FIG. 8 is a schematic diagram illustrating a specific content of processing for determining extraction target words.

The second information obtainment unit 24 analyzes, by using a keyword table 24A, the first information J1 obtained by the first information obtainment unit 23, and determines an extraction target word that is used as a factor for determining a slice position. FIG. 8 is a schematic diagram illustrating an example of the specific content of processing. As illustrated in FIG. 8, in the keyword table 24A, extraction target words are divided into groups of related words. The keyword table 24A registers, as the extraction target words, information about an anatomical structure and/or a lesion. The second information obtainment unit 24 searches the first information J1 obtained by the first information obtainment unit 23 for an extraction target word registered in the keyword table 24A. For example, when the first information J1 includes the term "lung" and the term "node", "lung, lung field, right lung, left lung, upper lobe, middle lobe, lower lobe (inferior lobe), . . . " and "node" are determined as the extraction target words.

The method for determining the extraction target words is not limited to the aforementioned method. For example, a known natural language processing technique or the like, which is used in a search engine, may be used. When an image reading report is prepared, if the name of the anatomical structure or the lesion is standardized, for example, by providing a user interface for inputting the anatomical structure or the lesion or the like by selecting names or the like, a sufficient effect is achieved also in search using the keyword table. When the extraction target word is determined, it is not necessary that the keyword table 24A is used. A term that is included in the first information J1 obtained by the first information obtainment unit 23 may be used directly without using the keyword table 24A.

Then, the second information obtainment unit 24 analyzes information about the finding (the content displayed in the finding area 54 in FIG. 7) in the image reading report RPT to which the patient ID of the same patient as the first tomographic image D1 is provided, and obtains, as second information J2, an extraction target word or words. For example, when the finding includes the expression "node of 3 cm in diameter is present in upper lobe S2 of left lung", the term "upper lobe of left lung" and the term "node" are obtained, as the second information J2, from the finding.

The image determination unit 25 determines an image in the image reading report RPT from which the second information J2 has been obtained, the image linked to a keyword in the finding, as an image G2 at a corresponding slice position, which corresponds to the slice position determined by the image determination unit 25. Here, slice positions in a predetermined range with respect to the slice position of the image linked to the keyword in the finding in the image reading report RPT from which the second information J2 has been obtained maybe set as a search range. Further, correlation between the images at the slice positions in the search range and the image at the target slice position may be calculated, and an image at a slice position that has a highest correlation with the target slice position may be determined as the image G2 at the corresponding slice position.

Meanwhile, the image obtainment unit 21 obtains link information IL from the image reading report RPT from which the second information J2 has been extracted. The link information IL is used to access an image at the corresponding slice position. As described in the section about the image reading report database 8, the link information IL is correlated with the image reading report database 8 together with other information in the image reading report RPT. Therefore, when the workstation 4 for the clinical department obtains an image reading report from the image reading report server 7, the workstation 4 for the clinical department obtains the link information IL together with the image reading report RPT. Then, the image obtainment unit 21 sends a retrieval request to the image information management server 5 based on the link information IL, and obtains an image G2 at the corresponding slice position from the second tomographic image D2.

The display screen generation unit 26 generates a display screen SC for comparison image reading in which an image G1 at a slice position determined by the slice position determination unit 22 and an image G2 at a corresponding slice position are laid out (displayed). The generated display screen SC is displayed on a display monitor at the workstation 4 for the clinical department.

Figure 11:
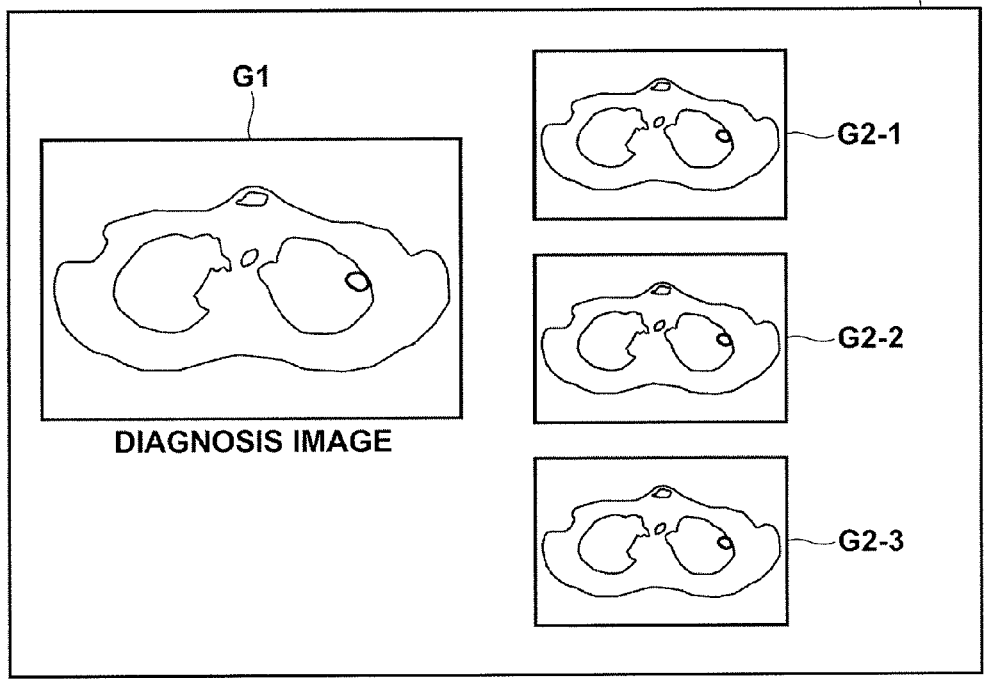
FIG. 11 is a diagram illustrating an example of a display screen for comparison image reading (No. 3)

FIG. 9 is a diagram illustrating an example of a display screen for comparison image reading. As illustrated in FIG. 9, in a display screen 60, an image at a slice position determined by the slice position determination unit 22, in other words, the image (diagnosis image) G1 at the slice position of the image reading target specified by the user and an image (reference image) G2 at a corresponding slice position are displayed together, for example, next to each other. When examination was performed on the same patient a plurality of times, a plurality of images at the corresponding slice position are obtained in some cases. In such cases, the plurality of corresponding slice images G2 may be displayed in a switchable manner, for example, by pressing a space key on the keyboard. Alternatively, as illustrated in FIG. 10, a list 61 of information identifying a plurality of images at the corresponding slice position may be displayed together with the image G1 at the slice position of the image reading target. After the user selects an image to be displayed from the list, the image G1 at the target slice position and the image G2 at the corresponding slice position may be displayed together, for example, next to each other. It is desirable to use, as the information for identifying the plurality of images at the corresponding slice position, the date of radiography and the kind of a modality, as illustrated in FIG. 10. Further, as illustrated in FIG. 11, reduced images G2-1 through G2-3, which are obtained by reducing the plurality of images at the corresponding slice position, may be displayed together with the image G1. After the user selects a desirable reduced image from the reduced images G2-1 through G2-3 by clicking or the like, the selected reduced image may be enlarged. Further, the image G1 at the target slice position and the enlarged selected image G2 at the corresponding slice position may be displayed together, for example, next to each other.

Figure 12:
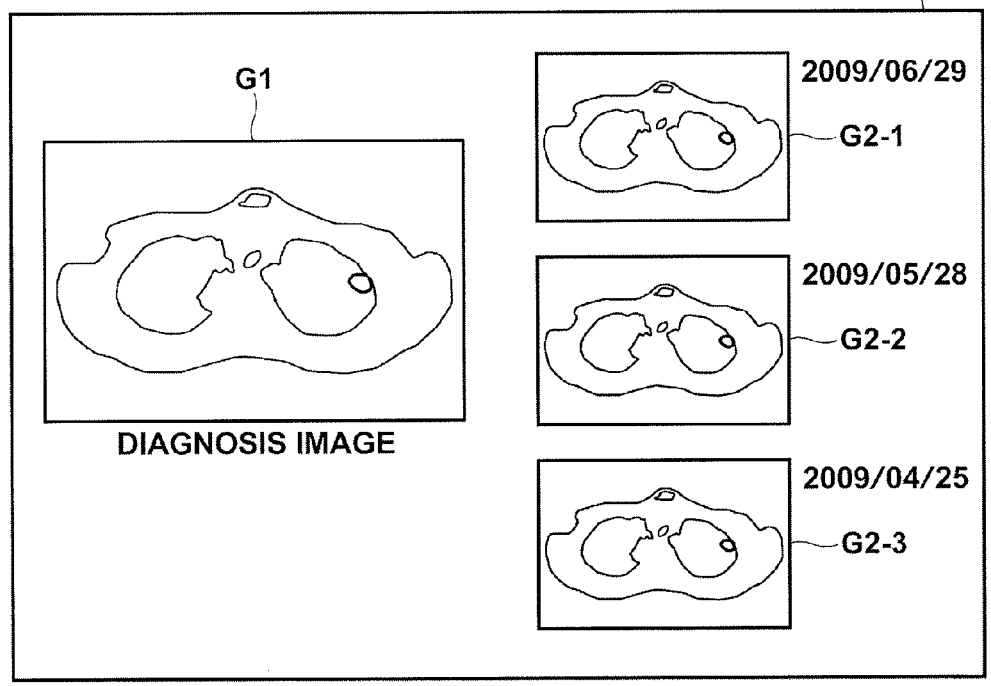
FIG. 12 is a diagram illustrating an example of a display screen for comparison image reading (No. 4)

Further, as illustrated in FIG. 12, reduced images G2-1 through G2-3, which are obtained by reducing the plurality of images at the corresponding slice position, may be displayed together with the image G1. Further, the dates of radiography of the reduced images G2-1 through G2-3 may be displayed.

Figure 13:
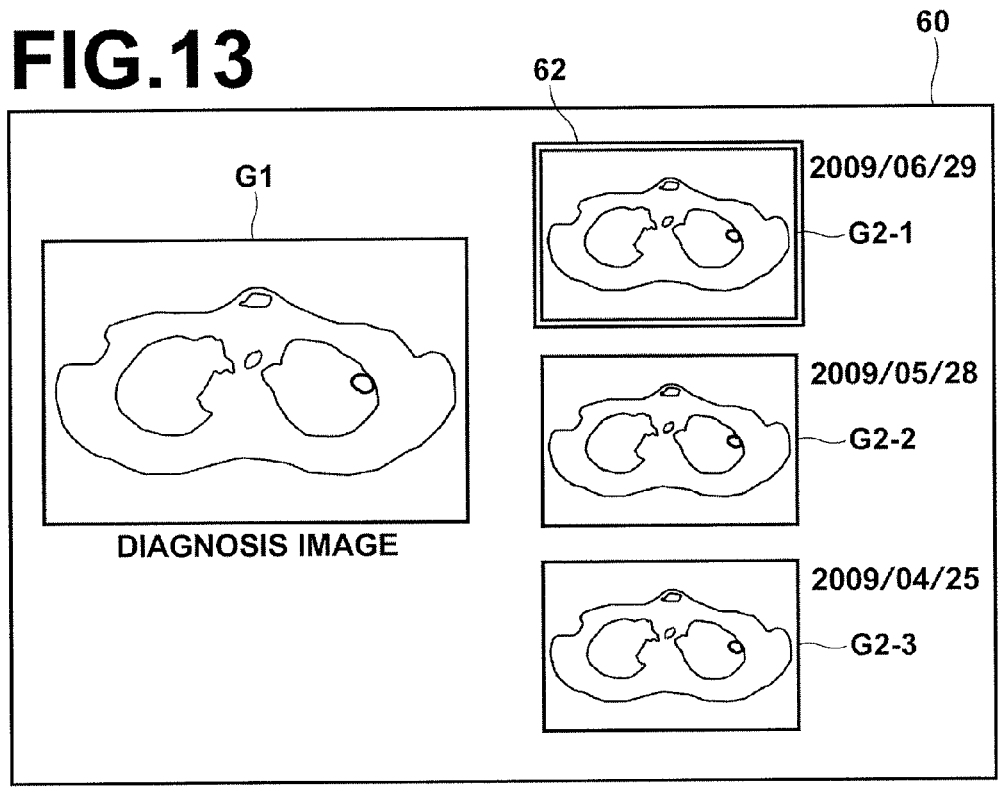
FIG. 13 is a diagram illustrating an example of a display screen for comparison image reading (No. 5)
Figure 14:
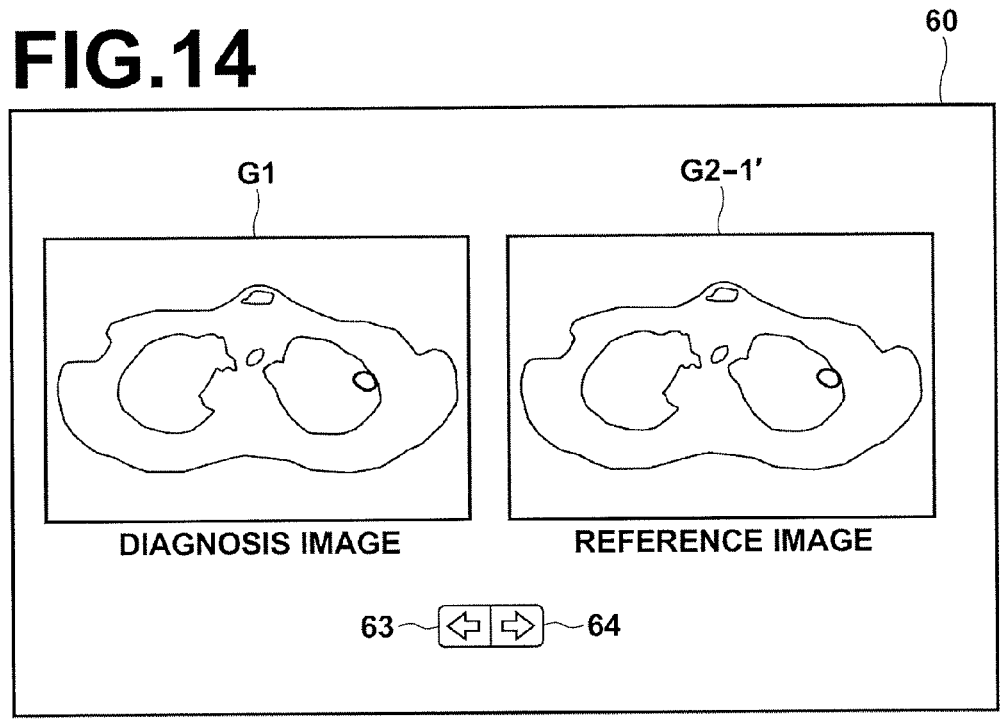
FIG. 14 is a diagram illustrating an example of a display screen for comparison image reading (No. 6)

In this case, the reduced images G2-1 through G2-3 should be displayed in a chronological order of radiography from the most recently obtained image. Further, as illustrated in FIG. 13, the reduced image G2-1, which was most recently obtained by radiography, may be displayed initially in a selected state. Accordingly, it becomes possible to easily select the reduced image of the most recently obtained radiographic image. In FIG. 13, a frame 62 is provided around the reduced image G2-1 to indicate that the reduced image G2-1 is initially selected. Alternatively, as illustrated in FIG. 14, the reduced image G2-1 of the most recently radiographed image may be enlarged to the same size as the diagnosis image G1 and displayed, as reference image G2-1'. Further, the displayed reference image G2-1' may be switched to reference images G2-2' and G2-3', which correspond to the other reduced images G2-2 and G2-3, by the switch buttons 63 and 64.

Figure 15:
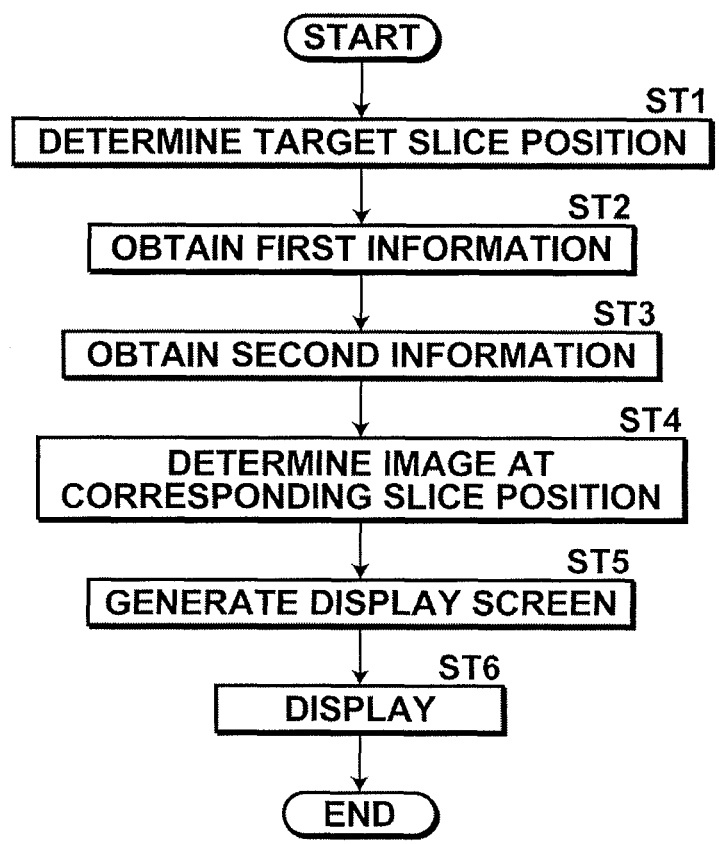
FIG. 15 is a flow chart of processing performed at a workstation for a clinical department in the first embodiment.

Next, processing performed in the first embodiment will be described. FIG. 15 is a flow chart of processing performed at the workstation 4 for the clinical department in the first embodiment. While an image at a slice position of an image reading target is displayed, if the user presses the comparison image reading start button 37, a software program for realizing an image viewing function is started. Further, the slice position determination unit 22 determines, as a target slice position, the slice position of an image that is currently displayed (step ST1). Then, the first information obtainment unit 23 obtains first information J1 from the first tomographic image D1 or by an input by a user (step ST2). Then, the second information obtainment unit 24 obtains, as second information J2, an extraction target word corresponding to the first information J1 (step ST3). The second information obtainment unit 24 obtains the extraction target word from the image reading report RPT. Further, the image determination unit 25 determines, as an image G2 at a corresponding slice position, an image correlated with the image reading report RPT from which the second information J2 has been obtained (step ST4). The corresponding slice position corresponds to the target slice position.

Further, the display screen generation unit 26 generates a display screen SC including the image G1 at the target slice position and the image G2 at the corresponding slice position (step ST5). The display screen SC is displayed on a display monitor at the workstation 4 for the clinical department (step ST6), and processing ends.

As described above, in the first embodiment, information about an anatomical structure and/or a lesion related to the first information J1 is obtained, as the second information J2, from the image reading report RPT. Further, an image correlated with the image reading report RPT from which the second information J2 has been obtained is determined as the image G2 at the corresponding slice position, which corresponds to the target slice position. Therefore, compared with the method of identifying the slice position by image processing, as disclosed in Patent Document 1, it is possible to accurately identify images at the same slice position in the first tomographic image and the second tomographic image.

When the image reading report RPT is prepared, a representative image, which most clearly and noticeably represents the finding in image reading, is used. In this case, an image that is correlated with a keyword included in the text of the finding in the image reading report is the representative image. In the first embodiment, when the first information obtainment unit 23 automatically obtains the first information J1, a lesion may be detected in an image at a different slice position from a target slice position in the second tomographic image D2 in some cases. In such cases, an image from which the first information J1 is obtained differs from the image at the target slice position. Meanwhile, in the second tomographic image D2, the representative image is correlated with the keyword in the text of the finding in the image reading report. Therefore, when the first information J1 obtained by the first information obtainment unit 23 is used, the slice position of the image correlated with the image reading report RPT from which the second information J2 has been obtained differs from the target slice position.

However, even in such a case, when the first information J1 has been obtained, it is possible to recognize a difference between the slice position of the first tomographic image D1 from which the first information J1 has been obtained and the target slice position. In this case, the slice position of the image correlated with the image reading report RPT from which the second information J2 has been extracted is the same as the slice position of the image from which the first information J1 has been obtained. Therefore, it is possible to identify the corresponding slice position based on the difference between the slice position of the image from which the first information J1 was obtained and the target slice position. For example, when the difference between the slice position of the image from which the first information J1 was obtained and the target slice position is +1 cm, the corresponding slice position is away by +1 cm from the slice position of the image correlated with the image reading report from which the second information J2 was obtained. When the corresponding slice position is determined in such a manner, it is possible to accurately identify the same slice position in the first tomographic image and in the second tomographic image.

Figure 16:
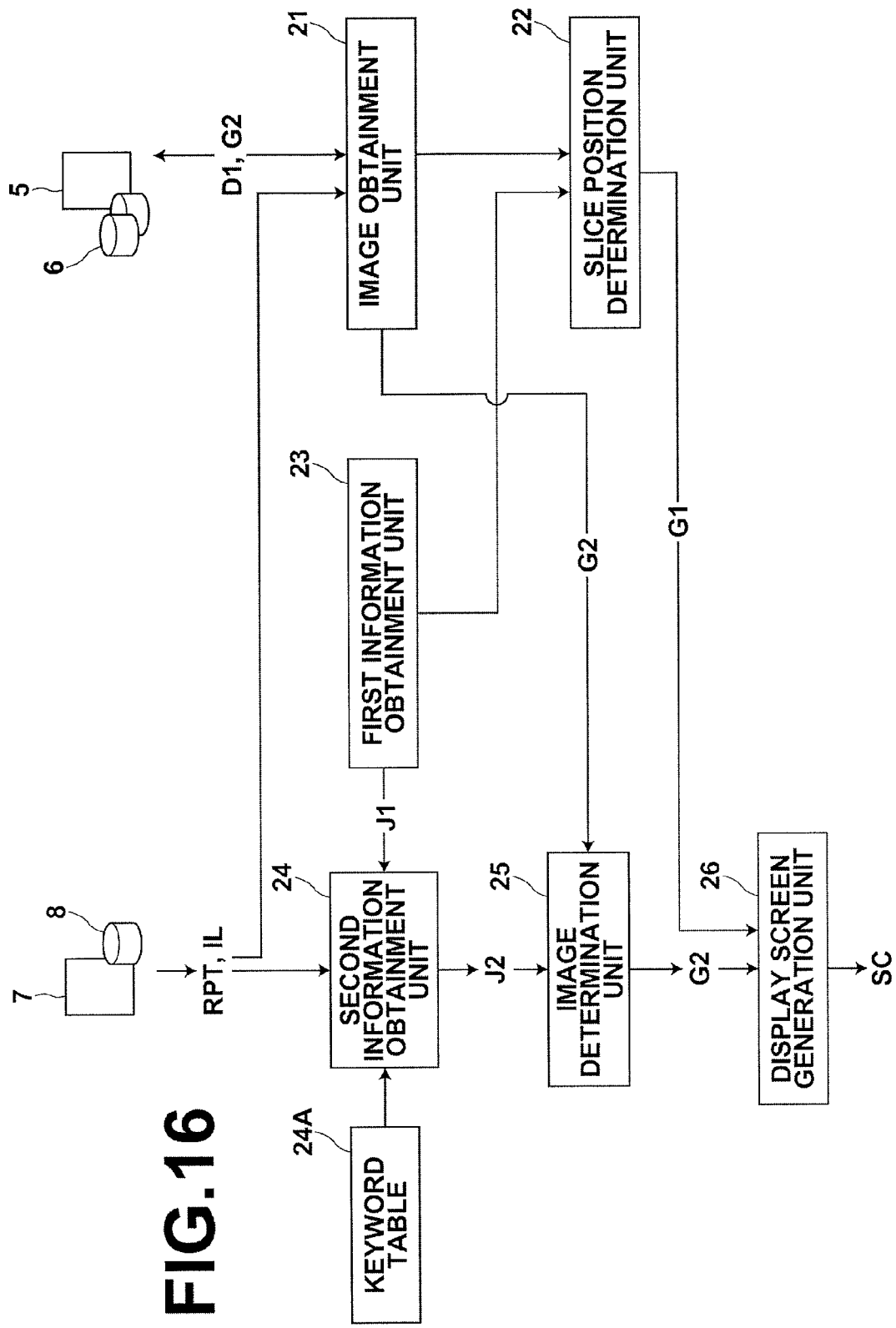
FIG. 16 is a schematic block diagram illustrating the configuration of a medical image display apparatus to which a medical image processing apparatus according to a second embodiment of the present invention has been applied, and which is installed as an image viewing function in a workstation for a clinical department, and the flow of data in the medical image display apparatus.

Next, a second embodiment of the present invention will be described. FIG. 16 is a schematic block diagram illustrating the configuration of a medical image display apparatus to which the medical image processing apparatus according to the second embodiment of the present invention has been applied, and which is installed as an image viewing function in the workstation 4 for the clinical department, and the flow of data in the medical image display apparatus. The second embodiment of the present invention differs from the first embodiment of the present invention in that the first information J1 is obtained from the image reading report RPT related to the first tomographic image in the second embodiment. The second embodiment will be described, focusing on the difference from the first embodiment.

A software program for realizing the image viewing function in the second embodiment is started by the user by retrieving an image reading report and by performing an operation for comparison image reading in a display screen of an image correlated with the image reading report. Here, a link is provided in the image reading report to correlate a keyword in the text of the finding to an image that should be referred to together with the keyword. Therefore, when the user displays the image reading report RPT, as illustrated in FIG. 7, and specifies a keyword in the text of the finding by clicking or the like, it is possible to display the image linked to the keyword in the display screen 30 (please refer to FIG. 3) of the diagnosis target image. In the second embodiment, when the comparison image reading start button 37 in the display screen 30 is pressed, the software program for realizing the image viewing function is started in a manner similar to the first embodiment.

When the software program is started, the slice position determination unit 22 determines, as the target slice position of comparison target, the slice position of an image that is currently displayed. Next, the first information obtainment unit 23 obtains, as the first information J1, a keyword included in the text of the finding in the image reading report which had been referred to before the currently displayed image was displayed. For example, in the image reading report RPT illustrated in FIG. 7, the keyword "upper lobe of left lung" and the keyword "node" are obtained as the first information J1.

Then, the second information obtainment unit 24 accesses the image reading report server 7, and obtains, as the second information J2, an extraction target word corresponding to the first information J1 from the image reading report RPT of the second tomographic image D2 in a manner similar to the first embodiment. Further, the image determination unit 25, the image obtainment unit 21, and the display screen generation unit 26 determine the image at the corresponding slice position, obtain the image at the corresponding slice position, and generate the display screen SC in a manner similar to the first embodiment.

As described above, compared with the method of identifying the slice position by image processing, as disclosed in Patent Document 1, it is possible to accurately identify images at the same slice position in the first tomographic image and in the second tomographic image also in the second embodiment in a manner similar to the first embodiment.

Figure 17:
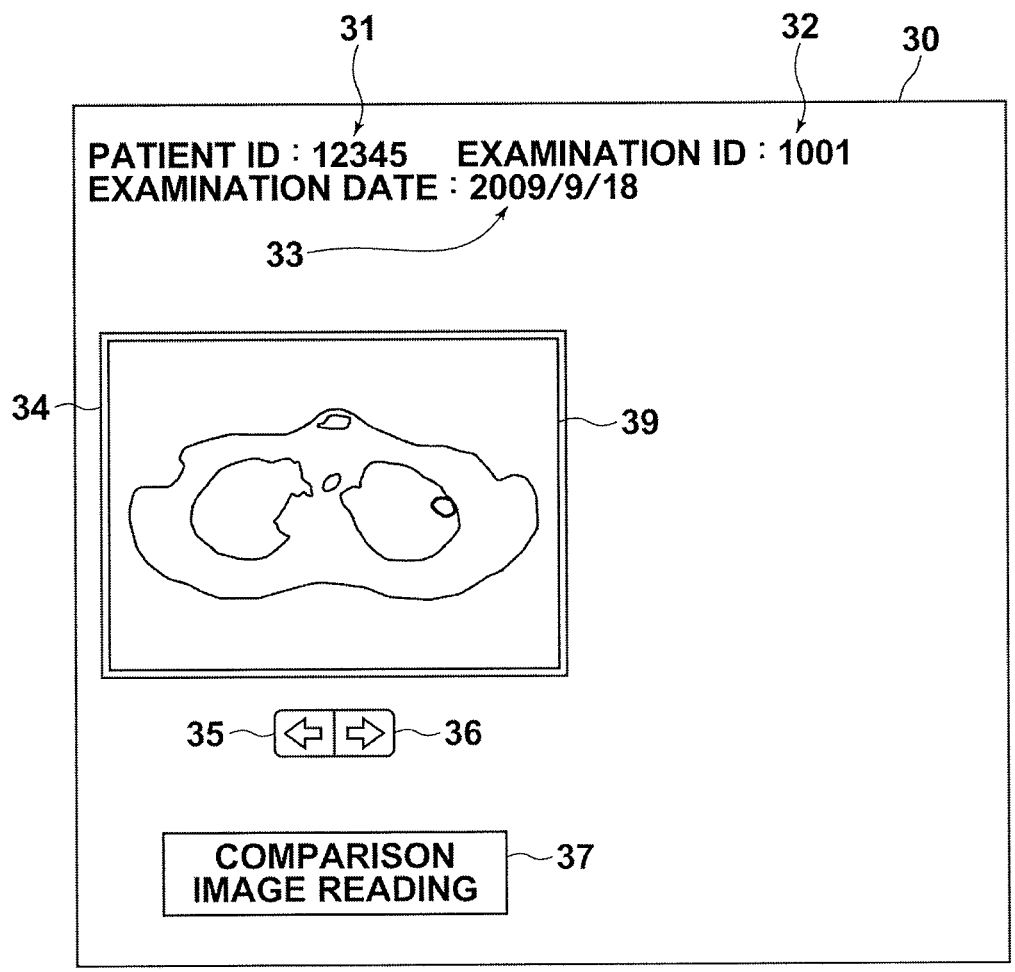
FIG. 17 is a diagram illustrating a display screen of an image in the second embodiment.

In the second embodiment, the image reading report RPT illustrated in FIG. 7 is displayed, and the keyword in the text of the finding is specified by clicking or the like, and an image linked to the keyword is displayed in the display screen 30 of the diagnosis target image. Alternatively, the display screen 30 may be displayed in advance. In that case, when an image at a slice position of an image reading target displayed in the area 34 is linked to the keyword in the text of the finding in the image reading report RPT, a frame 39 may be displayed around the image displayed in the area 34, as illustrated in FIG. 17, so that it is possible to distinguish that the image is linked to the image reading report RPT. Alternatively, a mark may be provided in a part of the image displayed in the area 34 instead of the frame 39. Accordingly, when the frame 39 or the image to which a mark is provided is displayed in the area 34, the user can recognize that the image is linked to the image reading report RPT. The user should press the comparison image reading start button 37 while the image is displayed. Accordingly, the software program for realizing the image viewing function is started, and the target slice position is determined. Further, the image at the corresponding slice position is determined, and an image at the corresponding slice position is obtained. Further, a display screen is generated.

Further, a virtual endoscopic image similar to an endoscopic image may be generated from a multi-slice tomographic image. In the first embodiment and the second embodiment, a virtual endoscopic image that is generated from the first tomographic image may be displayed in the area 34 of the display screen 30 instead of the first tomographic image. In this case, the virtual endoscopic image is, for example, a motion image (video) representing the state of imaging the body cavity of a subject (patient) while the viewpoint of the endoscope is moved. The user may display the virtual endoscopic image in the area 34 while changing the viewpoint position. Further, while a virtual endoscopic image at a viewpoint position of the image reading target, the image including a lesion or the like, is displayed, the user may press the comparison image reading button 37 to start the software program for realizing the image viewing function. As the image of the target of comparison image reading, a tomographic image may be used in a manner similar to the first embodiment and the second embodiment.

When comparison image reading using a virtual endoscopic image and a tomographic image is applied to the first embodiment, the viewpoint position of the currently-displayed virtual endoscopic image is determined as a target viewpoint position of the image reading target. Then, the first information is obtained, and the second information is obtained, and an image at a corresponding slice position, which corresponds to the target viewpoint position, is determined. Further, a display screen for comparison image reading is generated and displayed. Meanwhile, when the comparison image reading using a virtual endoscopic image and a tomographic image is applied to the second embodiment, first information is obtained from an image reading report related to the currently-displayed virtual endoscopic image. Second information is obtained, and an image at a corresponding slice position, which corresponds to the target viewpoint position, is determined. Further, a display screen for comparison image reading is generated, and displayed.

Figure 18:
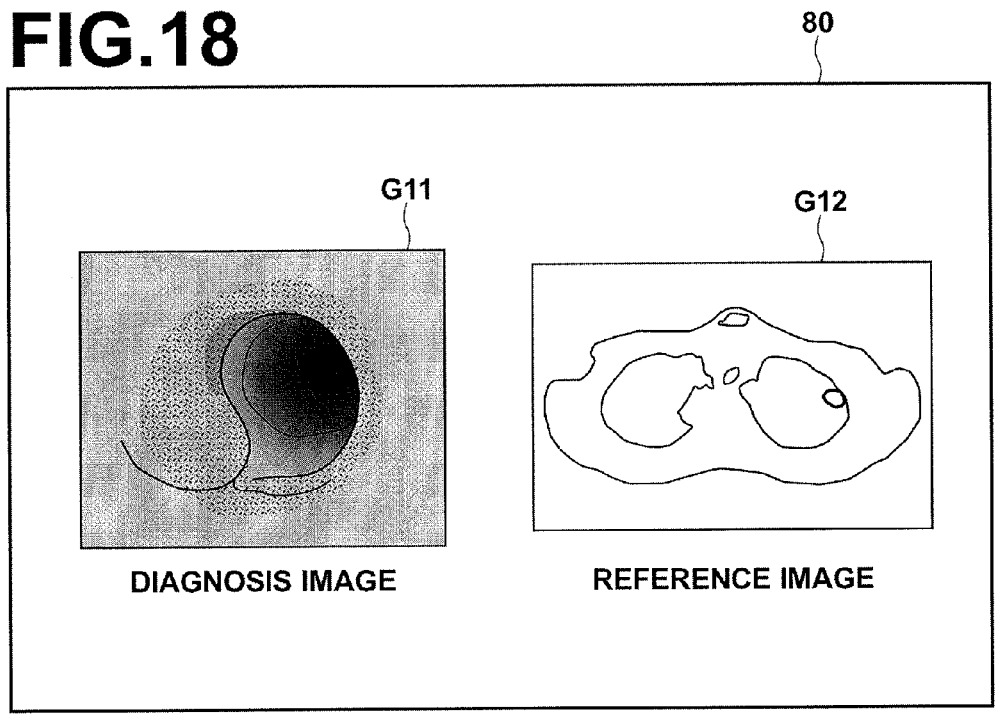
FIG. 18 is a diagram illustrating an example of a display screen for comparison image reading when a virtual endoscopic image and a tomographic image are used.

FIG. 18 is a diagram illustrating an example of a display screen for comparison image reading when a virtual endoscopic image and a tomographic image are used. As illustrated in FIG. 18, a display screen 80 displays a virtual endoscopic image (diagnosis image) G11 at a viewpoint position of the image reading target specified by the user and an image (reference image) G12 at a corresponding slice position together, for example, next to each other. When a plurality of images at the corresponding position are obtained, the display screen may be generated and displayed in a manner similar to the display screens illustrated in FIGS. 10 through 14.

Further, the target of comparison image reading is not limited to a tomographic image. A past endoscopic image of the same patient, which was obtained in real endoscopy, may be used. In this case, when a lesion or the like is detected during observation of the body cavity of the patient by using an endoscope, an endoscopic image at the position (at which the lesion or the like was observed) is clipped to obtain a still endoscopic image. The doctor prepares an image reading report by using the still endoscopic image, and registers the image reading report in the image reading report server 7. In this case, the image reading report and the still endoscopic image are linked to each other.

Therefore, when comparison image reading using the virtual endoscopic image and the still endoscopic image is applied to the first embodiment, the viewpoint position of the currently-displayed virtual endoscopic image is determined as the target viewpoint position of the image reading target. Then, the first information is obtained, and the second information is obtained. Further, a still endoscopic image at a corresponding viewpoint position, which corresponds to the target viewpoint position, is determined. Further, a display screen for comparison image reading is generated, and displayed. Meanwhile, when the comparison image reading using the virtual endoscopic image and the still endoscopic image is applied to the second embodiment, the first information is obtained from the image reading report related to the currently-displayed virtual endoscopic image. Further, the second information is obtained, and the still endoscopic image at the corresponding viewpoint position, which corresponds to the target viewpoint position, is determined. Further, a display screen for comparison image reading is generated and displayed.

Figure 19:
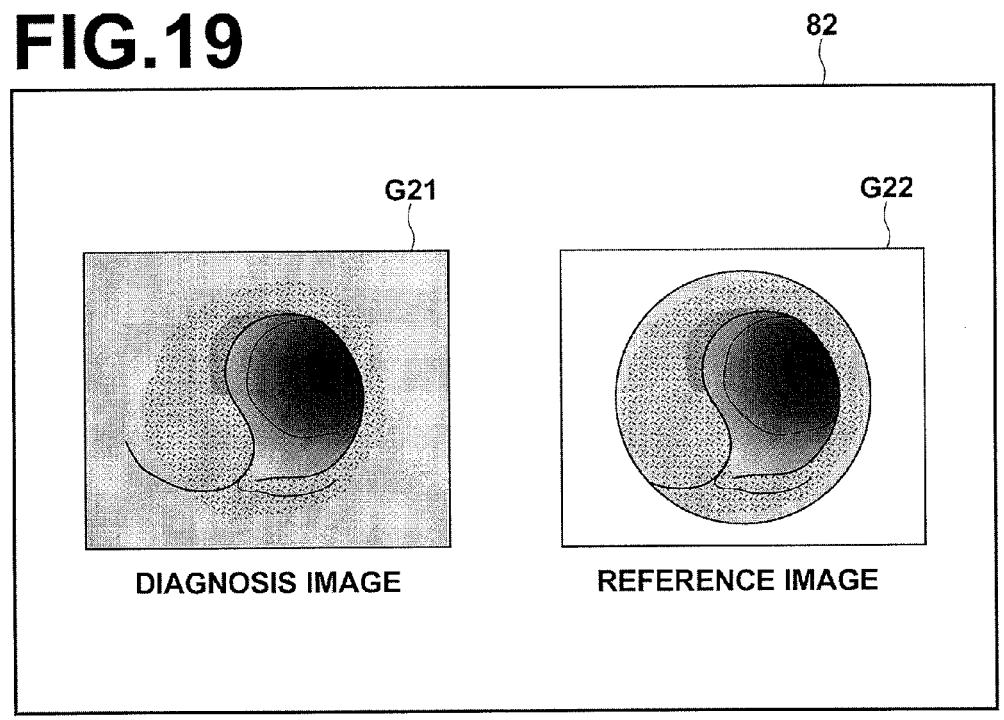
FIG. 19 is a diagram illustrating an example of a display screen for comparison image reading when a virtual endoscopic image and a still endoscopic image are used.

FIG. 19 is a diagram illustrating an example of a display screen for comparison image reading when a virtual endoscopic image and a still endoscopic image are used. As illustrated in FIG. 19, a display screen 82 displays a virtual endoscopic image (diagnosis image) G21 at a viewpoint position of the image reading target specified by the user and a still endoscopic image (reference image) G22 at a corresponding viewpoint position. The image G21 and the image G22 are displayed together, for example, next to each other. When a plurality of still endoscopic images at the corresponding viewpoint position are obtained, a display screen similar to the display screens illustrated in FIGS. 10 through 14 should be generated, and displayed.

In the above embodiments, the medical image processing apparatus of the present invention was applied to the workstation 4 for a clinical department. Alternatively, the medical image processing apparatus of the present invention may be applied to the workstation 3 for a radiology department.

What is claimed is:

1. A medical image processing apparatus comprising:
a target viewpoint position determination means that determines a position which is designated by a user as a target viewpoint position in a first medical image having multiple viewpoints;
a first information obtainment means that obtains, as first information, information about at least one of an anatomical structure and a lesion regarding first medical image from the first medical image;
a second information obtainment means that determines an extraction target word by analyzing the first information, and obtains, as second information, the extraction target word from image reading report information including a finding with respect to at least one second medical image of the same examined person as the first medical image, each of the at least one second medical image having multiple viewpoints and having been obtained at different time from obtainment of the first medical image, the image reading report information being linked to an image of a viewpoint position at which the finding was prepared; and
an image determination means that determines, based on the viewpoint position of the image linked to the image reading report information from which the second information has been obtained, an image of a corresponding viewpoint position, which corresponds to the target viewpoint position in the second medical image.

2. A medical image processing apparatus, as defined in claim 1, wherein the first information obtainment means obtains the first information from an image of the target viewpoint position in the first medical image.

3. A medical image processing apparatus comprising:
a target viewpoint position determination means that determines a position which is designated by a user as a target viewpoint position in a first medical image having multiple viewpoints;
a first information obtainment means that obtains, as first information, information about at least one of an anatomical structure and a lesion in a finding with respect to an image of the target viewpoint position from image reading report information including the finding;
a second information obtainment means that determines an extraction target word by analyzing the first information, and obtains, as second information, the extraction target word from image reading report information including a finding with respect to at least one second medical image of the same examined person as the first medical image, each of the at least one second medical image having multiple viewpoints and having been obtained at different time from obtainment of the first medical image, the image reading report information being linked to an image of a viewpoint position at which the finding was prepared; and
an image determination means that determines, based on the viewpoint position of the image linked to the image reading report information from which the second information has been obtained, an image of a corresponding viewpoint position, which corresponds to the target viewpoint position in the second medical image.

4. A medical image processing apparatus, as defined in claim 1, the apparatus further comprising:
a display control means that displays a display screen including an image of the target viewpoint position and the image of the corresponding viewpoint position on a display means.

5. A medical image processing apparatus, as defined in claim 4, wherein when the number of images of the corresponding viewpoint position is one, the display control means displays the display screen including the image of the corresponding viewpoint position on the display means.

6. A medical image processing apparatus, as defined in claim 4, wherein when the number of images of the corresponding viewpoint position is at least two, the display control means displays the display screen including a list of information for identifying the at least two images of the corresponding viewpoint position on the display means, and further displays, on the display means, an image of the corresponding viewpoint position identified in the list.

7. A medical image processing apparatus, as defined in claim 4, wherein when the number of images of the corresponding viewpoint position is at least two, the display control means displays the display screen including all images of the corresponding viewpoint position on the display means.

8. A medical image processing apparatus, as defined in claim 4, wherein when the number of images of the corresponding viewpoint position is at least two, the display control means displays the display screen in which all images of the corresponding viewpoint position are switchable on the display means.

9. A medical image processing apparatus, as defined in claim 7, wherein the display control means displays, on the display means, the display screen in such a manner that a most-recently-obtained image of the corresponding viewpoint position is in a selected state.

10. A medical image processing apparatus, as defined in claim 7, wherein the display control means displays the display screen including the date/time of obtainment of each of all the images of the corresponding viewpoint position on the display means.

11. A medical image processing apparatus, as defined in claim 1, wherein the image determination means identifies the viewpoint position of the image correlated with the image reading report information from which the second information has been obtained, and determines the image of the corresponding viewpoint position based on a correlation between an image of a viewpoint position in a predetermined range with respect to the identified viewpoint position and the image of the target viewpoint position.

12. A medical image processing apparatus, as defined in claim 1, wherein the first medical image having multiple viewpoints is a multi-slice tomographic image, and wherein the at least one second medical image each having multiple viewpoints is a multi-slice tomographic image.

13. A medical image processing apparatus, as defined in claim 1, wherein the first medical image having multiple viewpoints is a virtual endoscopic image generated from a multi-slice tomographic image, and wherein the at least one second medical image each having multiple viewpoints is a real endoscopic image or a multi-slice tomographic image.

14. A medical image processing method comprising the steps of:

determining a target viewpoint position as designated by a user in a first medical image having multiple viewpoints by using a processing apparatus;

obtaining, as first information, information about at least one of an anatomical structure and a lesion in the first medical image from the first medical image;

determining an extraction target word by analyzing the first information;

obtaining, as second information, the extraction target word from image reading report information including a finding with respect to at least one second medical image of the same examined person as the first medical image, each of the at least one second medical image having multiple viewpoints and having been obtained at different time from obtainment of the first medical image, the image reading report information being linked to an image of a viewpoint position at which the finding was prepared; and determining, based on the viewpoint position of the image linked to the image reading report information from which the second information has been obtained, an image of a corresponding viewpoint position, which corresponds to the target viewpoint position in the second medical image.

15. A medical image processing method comprising the steps of:

determining a target viewpoint position as designated by a user in a first medical image having multiple viewpoints by using a processing apparatus;

obtaining, as first information, information about at least one of an anatomical structure and a lesion in a finding with respect to an image of the target viewpoint position from image reading report information including the finding;

determining an extraction word target by analyzing the first information;

obtaining, as second information, the extraction target word from image reading report information including a finding with respect to at least one second medical image of the same examined person as the first medical image, each of the at least one second medical image having multiple viewpoints and having been obtained at different time from obtainment of the first medical image, the image reading report information being linked to an image of a viewpoint position at which the finding was prepared; and determining, based on the viewpoint position of the image linked to the image reading report information from which the second information has been obtained, an image of a corresponding viewpoint position, which corresponds to the target viewpoint position in the second medical image.

16. A non-transitory computer-readable recording medium having stored therein a program that causes a computer to execute the procedures of:

determining a target viewpoint position designated by a user in a first medical image having multiple viewpoints;

obtaining, as first information, information about at least one of an anatomical structure and a lesion regarding first medical image from the first medical image;

determining an extraction word target by analyzing the first information;

obtaining, as second information, the extraction target word from image reading report information including a finding with respect to at least one second medical image of the same examined person as the first medical image, each of the at least one second medical image having multiple viewpoints and having been obtained at different time from obtainment of the first medical image, the image reading report information being linked to an image of a viewpoint position at which the finding was prepared; and determining, based on the viewpoint position of the image linked to the image reading report information from which the second information has been obtained, an image of a corresponding viewpoint position, which corresponds to the target viewpoint position in the second medical image.

17. A non-transitory computer-readable recording medium having stored therein a program that causes a computer to execute the procedures of:

determining a target viewpoint position as designated by a user in a first medical image having multiple viewpoints;

obtaining, as first information, information about at least one of an anatomical structure and a lesion in a finding with respect to an image of the target viewpoint position from image reading report information including the finding;

determining an extraction target word by analyzing the first information;

obtaining, as second information, the extraction target word from image reading report information including a finding with respect to at least one second medical image of the same examined person as the first medical image, each of the at least one second medical image having multiple viewpoints and having been obtained at different time from obtainment of the first medical image, the image reading report information being linked to an image of a viewpoint position at which the finding was prepared; and determining, based on the viewpoint position of the image linked to the image reading report information from which the second information has been obtained, an image of a corresponding viewpoint position, which corresponds to the target viewpoint position in the second medical image.

* * * * *